(12) United States Patent
De Sarkar et al.

(10) Patent No.: US 12,180,072 B2
(45) Date of Patent: *Dec. 31, 2024

(54) CHEMICAL SYNTHESIS PLANT

(71) Applicant: HALDOR TOPSØE A/S, Kgs. Lyngby (DK)

(72) Inventors: Sudip De Sarkar, Kokkedal (DK); Thomas Sandahl Christensen, Kgs. Lyngby (DK); Martin Østberg, Tune (DK); Kim Aasberg-Petersen, Allerød (DK)

(73) Assignee: HALDOR TOPSØE A/S, Kgs. Lyngby (DK)

(*) Notice: Subject to any disclaimer, the term of this patent is extended or adjusted under 35 U.S.C. 154(b) by 0 days.

This patent is subject to a terminal disclaimer.

(21) Appl. No.: 18/190,192

(22) Filed: Mar. 27, 2023

(65) Prior Publication Data

US 2023/0234842 A1   Jul. 27, 2023

Related U.S. Application Data

(63) Continuation of application No. 17/420,501, filed as application No. PCT/EP2020/059872 on Apr. 7, 2020, now Pat. No. 11,649,163.

(30) Foreign Application Priority Data

Apr. 8, 2019 (DK) .......................... PA 2019 00430

(51) Int. Cl.
*C01B 3/12* (2006.01)
*C01B 3/36* (2006.01)
*C01B 3/38* (2006.01)

(52) U.S. Cl.
CPC ................. *C01B 3/12* (2013.01); *C01B 3/36* (2013.01); *C01B 3/382* (2013.01);
(Continued)

(58) Field of Classification Search
CPC .. C07C 3/12; C07C 3/36; C07C 3/382; C07C 2203/0244; C07C 2203/061;
(Continued)

(56) References Cited

U.S. PATENT DOCUMENTS

| 2007/0244208 A1* | 10/2007 | Shulenberger ......... C10K 3/026 518/726 |
| 2022/0081289 A1 | 3/2022 | De Sarkar et al. |
| 2022/0081292 A1 | 3/2022 | De Sarkar et al. |

FOREIGN PATENT DOCUMENTS

| CA | 2872194 A1 | 3/2016 |
| EP | 2594527 A1 | 5/2013 |

(Continued)

OTHER PUBLICATIONS

Danish Search Report mailed on Sep. 30, 2019 by the Danish Patent and Trademark Office for Danish Patent Application No. PA 2019 00434. (9 pages).

(Continued)

*Primary Examiner* — Jafar F Parsa
(74) *Attorney, Agent, or Firm* — Boone IP Law

(57) ABSTRACT

A plant, such as a hydrocarbon plant, is provided, which has a syngas stage for syngas generation and a synthesis stage where the syngas is synthesized to produce syngas derived product, such as hydrocarbon product. The plant makes effective use of various streams; in particular $CO_2$ and $H_2$. The plant does not comprise an external feed of hydrocarbons. A method for producing a product stream, such as a hydrocarbon product stream is also provided.

20 Claims, 10 Drawing Sheets

Figure 1:
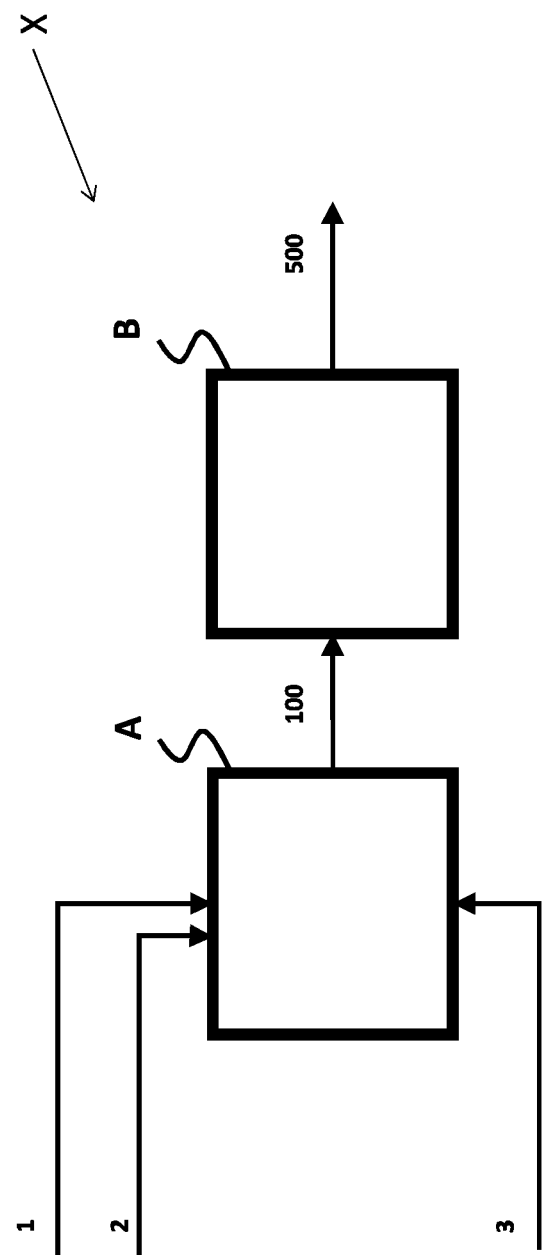

(52) U.S. Cl.
CPC ............... *C01B 2203/0244* (2013.01); *C01B 2203/0283* (2013.01); *C01B 2203/061* (2013.01); *C01B 2203/062* (2013.01); *C01B 2203/14* (2013.01)

(58) Field of Classification Search
CPC ........ C07C 2203/0445; C07C 2203/06; C01B 3/12; C01B 3/36; C01B 3/382; C01B 2203/0244; C01B 2203/061; C01B 2203/0445; C01B 2203/06; C10G 2/32
See application file for complete search history.

(56) References Cited

FOREIGN PATENT DOCUMENTS

| | | |
|---|---|---|
| WO | 9919277 A1 | 4/1999 |
| WO | 0001613 A1 | 1/2000 |
| WO | 2007108014 A1 | 9/2007 |
| WO | 2013189791 A1 | 12/2013 |
| WO | 2014057013 A1 | 4/2014 |
| WO | 2014096226 A1 | 6/2014 |
| WO | 2014154691 A1 | 10/2014 |
| WO | 2015128395 A1 | 9/2015 |
| WO | 2019020378 A1 | 1/2019 |
| WO | 2019020513 A1 | 1/2019 |
| WO | 2019020519 A1 | 1/2019 |

OTHER PUBLICATIONS

International Search Report (PCT/ISA/210) and Written Opinion (PCT/ISA/237) mailed on Jul. 10, 2020, by the European Patent Office as the International Searching Authority for International Application No. PCT/EP2020/059872. (12 pages).

International Search Report (PCT/ISA/210) and Written Opinion (PCT/ISA/237) mailed on Jul. 15, 2020, by the European Patent Office as the International Searching Authority for International Application No. PCT/EP2020/059598. (13 pages).

* cited by examiner

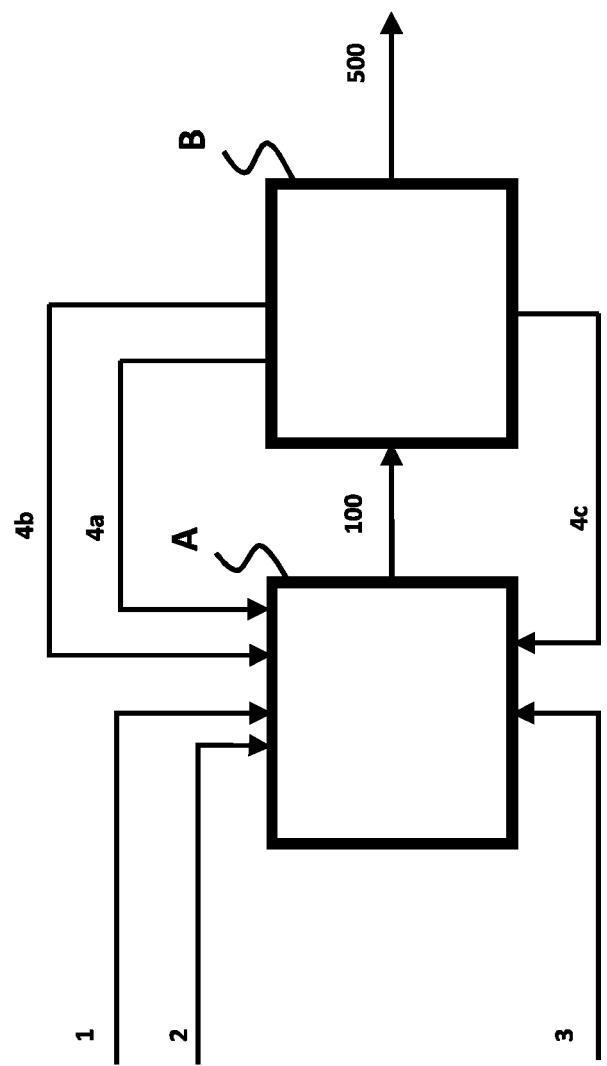

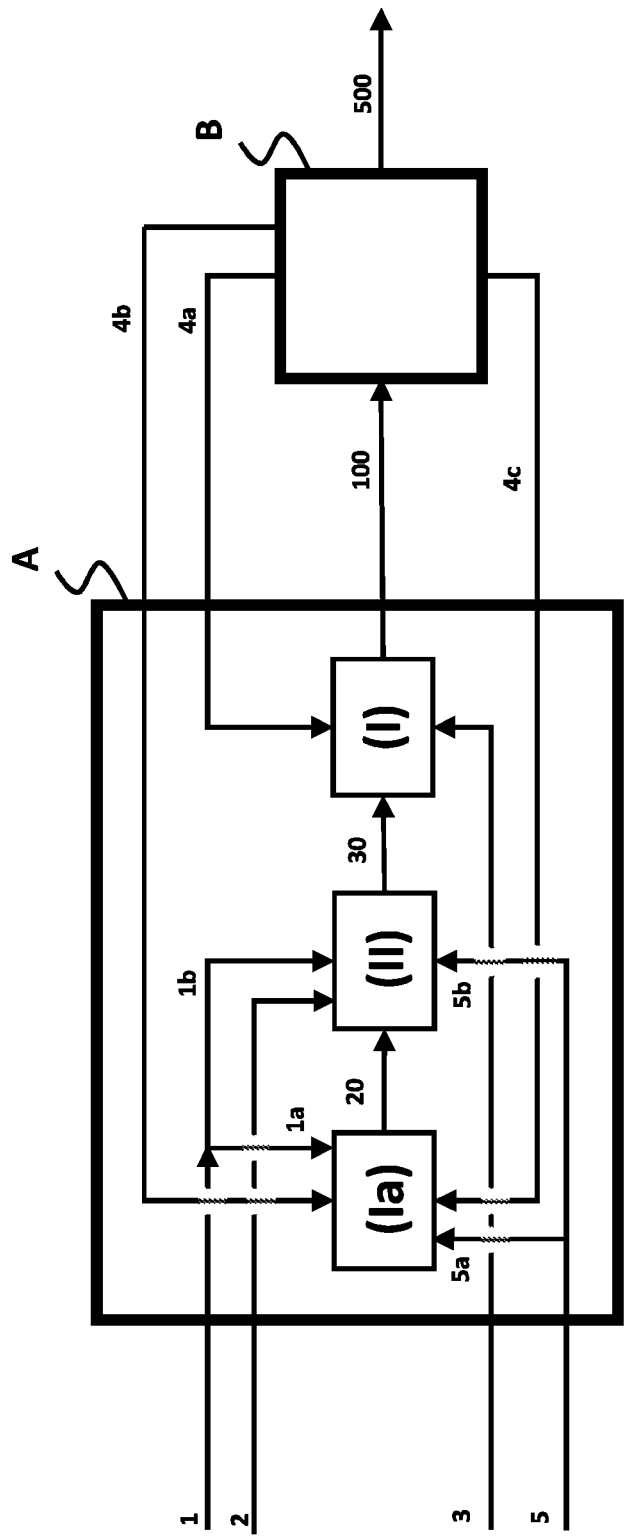

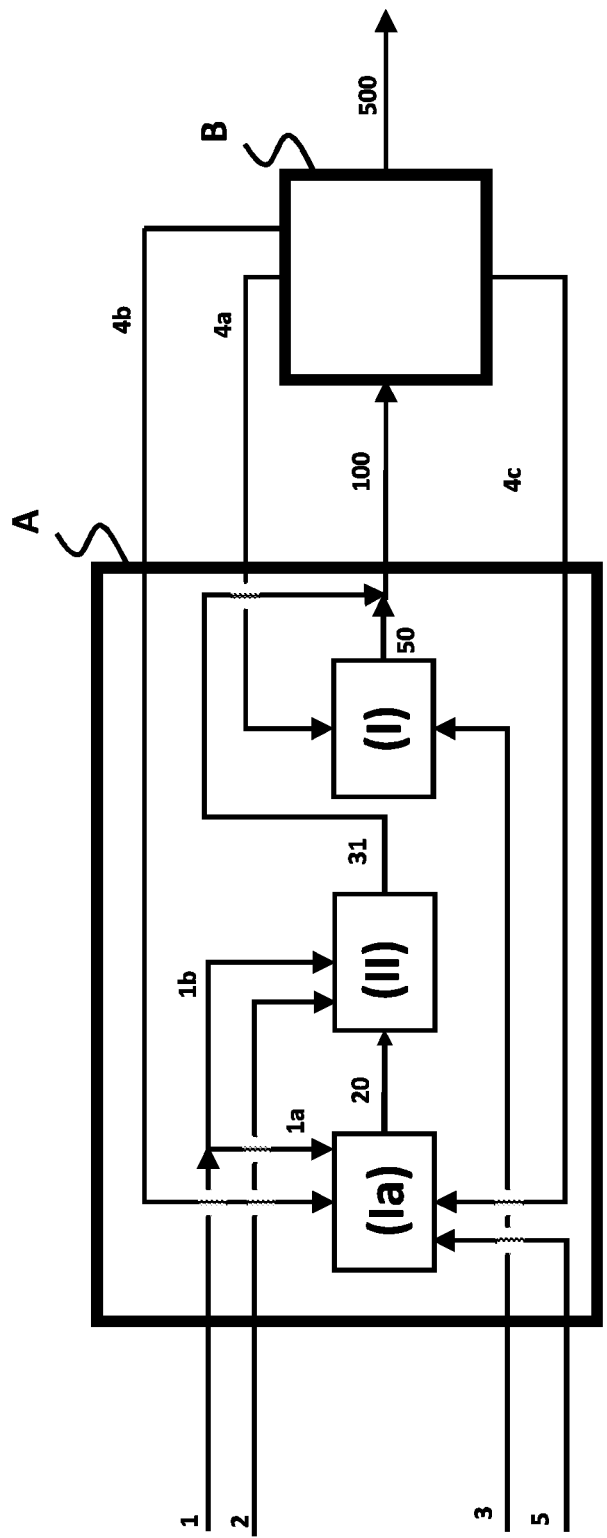

CHEMICAL SYNTHESIS PLANT

CROSS REFERENCE TO RELATED APPLICATIONS

The present application is a continuation of U.S. application Ser. No. 17/420,501, filed on Jul. 2, 2021, which is a U.S. national stage of international application no. PCT/EP2020/059872, filed on Apr. 7, 2020, which claims the benefit of Danish application no. PA 2019 00430, filed on Apr. 8, 2019. The entire contents of each of U.S. application Ser. No. 17/420,501, international application no. PCT/EP2020/059872, Danish application no. PA 2019 00430 are hereby incorporated herein by reference in their entirety.

TECHNICAL FIELD

The present invention relates to a plant, such as a hydrocarbon plant, with effective use of various streams, in particular carbon dioxide. A method for producing a product stream, such as a hydrocarbon product stream is also provided. The plant does not comprise an external feed of hydrocarbons. The plant and method of the present invention provide overall better utilization of carbon dioxide.

BACKGROUND

Carbon capture and utilization (CCU) has gained more relevance in the light of the rise of atmospheric $CO_2$ since the Industrial Revolution. In one way of utilizing $CO_2$, $CO_2$ and $H_2$ can be converted to synthesis gas (a gas rich in CO and $H_2$) which can be converted further to valuable products like alcohols (including methanol), fuels (such as gasoline, jet fuel, kerosene and/or diesel produced for example by the Fischer-Tropsch (F-T) process), and/or olefins etc.

Existing technologies focus primarily on stand-alone reverse Water Gas Shift (rWGS) processes to convert $CO_2$ and $H_2$ to synthesis gas. The synthesis gas can subsequently be converted to valuable products in the downstream processes as outlined above. The reverse water gas shift reaction proceeds according to the following reaction:

$$CO_2 + H_2 \leftrightarrow CO + H_2O \qquad (1)$$

The rWGS reaction (1) is an endothermic process which requires significant energy input for the desired conversion. Very high temperatures are needed to obtain sufficient conversion of carbon dioxide into carbon monoxide to make the process economically feasible. Undesired by-product formation of for example methane may also take place. High conversions of carbon dioxide can evidently also be obtained by high $H_2/CO_2$-ratio. However, this will often result in a synthesis gas with a (much) too high $H_2/CO$-ratio for the downstream synthesis.

Technologies relying on the rWGS reaction have other challenges. In some cases, internally recycled hydrocarbon streams may be available as co-feed. An example is the availability of hydrocarbons from a downstream synthesis stage (e.g., a propane and butane rich stream from an F-T stage; tail gas comprising different hydrocarbons from an F-T stage; naphtha stream from an F-T stage; propane and butane rich stream from a gasoline synthesis stage; a hydrocarbon stream from olefin synthesis etc.). Such hydrocarbons cannot be processed in an rWGS reactor. If the hydrocarbon streams from the downstream synthesis stage are not used at least in part for additional production of synthesis gas, the overall process may not be feasible from an economic point of view.

To address problems with existing technologies, a novel process of syngas preparation and then, synthesis from the said syngas to syngas derived product(s) from primarily $CO_2$, $H_2$ and $O_2$ feed is presented in this document. The proposed layout has at least the following advantages:

1. $CO_2$, $H_2$, and $O_2$ can be converted to syngas with a desired $H_2$:CO ratio, without using any external hydrocarbon feed to the plant.
2. Utilization of any hydrocarbon streams generated in the synthesis stage for synthesis gas production.
3. A higher utilization of the carbon dioxide feed is possible compared to a stand-alone rWGS section. One particular aim is to utilize more $CO_2$ feed instead of external hydrocarbon feed as a source of carbon.
4. If an electrolyser is used as part or all of the source of the hydrogen feed to the process, part or all of the oxygen, generated in the electrolyser along with $H_2$, can be used as the oxygen source that is required in the proposed process layout.

SUMMARY

In a first aspect, therefore, a plant is provided, comprising:
a. a syngas stage, said syngas stage comprising a methanation section and/or a reverse water gas shift (rWGS) section, and an autothermal reforming (ATR) section; and
b. a synthesis stage.

The plant further comprises:
a first feed comprising hydrogen to the syngas stage;
a second feed comprising carbon dioxide to the syngas stage;
a third feed comprising oxygen to the ATR section;
wherein said syngas stage is arranged to provide a syngas stream and feed said syngas stream to the synthesis stage; and wherein the plant does not comprise an external feed of hydrocarbons.

A method for producing a product stream, in particular a hydrocarbon product stream, using the above-described plant, is also provided.

Further details of the plant and the method are specified in the following detailed descriptions, figures and claims.

FIGURE LEGENDS

FIGS. 1-4 illustrate schematic layouts of various embodiments of a plant.

DETAILED DISCLOSURE

Unless otherwise specified, any given percentages for gas content are % by volume.

Specific Embodiments

As set out above, a plant—such as—a hydrocarbon plant is provided. The plant comprises:
a. a syngas stage, said syngas stage comprising a methanation section and/or a reverse water gas shift (rWGS) section and an autothermal reforming (ATR) section; and
b. a synthesis stage.

The plant comprises various feeds. For the avoidance of doubt, the term "feed"—when applied to a plant—refers to means for supplying said gas to the appropriate stage, reactor or unit, such as a duct, tubing etc. A first feed comprising hydrogen is provided to the syngas stage. Suitably, the first feed consists essentially of hydrogen. The first feed of hydrogen is suitably "hydrogen rich" meaning that the major portion of this feed is hydrogen, i.e., over 75%, such as over 85%, preferably over 90%, more preferably over 95%, even more preferably over 99% of this feed is hydrogen. One source of the first feed of hydrogen can be one or more electrolyser units. In addition to hydrogen the first feed may for example comprise steam, nitrogen, argon, carbon monoxide, carbon dioxide, and/or hydrocarbons. The first feed suitably comprises only low amounts of hydrocarbon, such as for example less than 5% hydrocarbons or less than 3% hydrocarbons or less than 1% hydrocarbons.

A second feed comprising carbon dioxide is provided to the syngas stage. Suitably, the second feed consists essentially of $CO_2$. The second feed of $CO_2$ is suitably "$CO_2$ rich" meaning that the major portion of this feed is $CO_2$, i.e., over 75%, such as over 85%, preferably over 90%, more preferably over 95%, even more preferably over 99% of this feed is $CO_2$. One source of the second feed of carbon dioxide can be one or more exhaust stream(s) from one or more chemical plant(s). One source of the second feed of carbon dioxide can also be carbon dioxide captured from one or more process stream(s) or atmospheric air. Another source of the second feed could be $CO_2$ captured or recovered from the flue gas for example from fired heaters, steam reformers, and/or power plants. The first and second feeds could be mixed before being added to the syngas stage. The second feed may in addition to $CO_2$ comprise for example steam, oxygen, nitrogen, oxygenates, amines, ammonia, carbon monoxide, and/or hydrocarbons. The second feed suitably comprises only low amounts of hydrocarbon, such as for example less than 5% hydrocarbons or less than 3% hydrocarbons or less than 1% hydrocarbons.

The ratio of $H_2:CO_2$ provided at the plant inlet varies from 1.0-9.0, preferably 2.5-8, more preferably 3.0-7.0. The actual ratio will depend upon the desired end product downstream the synthesis stage. This ratio is defined as any $H_2$ and $CO_2$ in external streams (i.e., not including hydrogen and/or carbon dioxide in any recycle streams).

The first and second feeds could be mixed before being added to the syngas stage.

When the synthesis stage is an FT synthesis stage, the desired $H_2/CO$-ratio of the synthesis gas will typically be around 2.0. Using a simplistic view, one unit of hydrogen is needed to convert each unit of $CO_2$ into CO. The addition of $O_2$ will also require some hydrogen and furthermore hydrogen will be needed as source of energy for auxiliary purposes such as for example generation of power. All in all, this means that for an FT synthesis stage the $H_2:CO_2$-ratio at the plant inlet (i.e., not including hydrogen and/or carbon dioxide in any recycle streams) should be in the range of 3.0-7.0 or more preferably from 3.0-6.0 and most preferably 3.0-5.0. If the desired end product is methanol or gasoline (via synthesis of methanol and the methanol-to-gasoline route) a similar consideration can be made and also in these cases the $H_2:CO_2$-ratio at the plant inlet should be in the range of 3.0-7.0 or more preferably from 3.0-6.0 and most preferably 3.0-5.0.

It should be noted that in some cases $H_2:CO_2$ ratios less than 3.0 such as between 2.0-3.0 can be utilized.

A third feed comprising oxygen is provided to the ATR section. Suitably, the third feed consists essentially of oxygen. The third feed of $O_2$ is suitably "$O_2$ rich" meaning that the major portion of this feed is $O_2$, i.e., over 75% such as over 90% or over 95%, such as over 99% of this feed is $O_2$. This third feed may also comprise other components such as nitrogen, argon, $CO_2$, and/or steam. This third feed will typically include a minor amount of steam (e.g., 5-10%). The source of third feed, oxygen, can be at least one air separation unit (ASU) and/or at least one membrane unit. The source of oxygen can also be at least one electrolyser unit. A part or all of the first feed, and a part or all of the third feed may come from at least one electrolyser. An electrolyser means a unit for converting steam or water into hydrogen and oxygen by use of electrical energy. Steam may be added to the third feed comprising oxygen, upstream the ATR section.

A hydrocarbon-containing off-gas stream (from the synthesis stage) may be fed to the syngas stage as a fourth feed comprising hydrocarbons. The source of fourth feed can be part or all of a stream comprising hydrocarbons produced in the synthesis stage. The fourth feed may additionally comprise other components such as $CO_2$ and/or CO and/or $H_2$ and/or steam and/or other components such as nitrogen and/or argon. Such a stream may comprise for example methane, ethane, propane, and/or butanes. Another example is Liquified Petroleum Gas (LPG) which is a stream rich in propane and butane. LPG may be produced for example in a gasoline synthesis unit or in a Fischer-Tropsch synthesis unit. Another example is a stream comprising naphtha which is produced in a synthesis stage for liquid fuel production via Fischer-Tropsch synthesis process. Suitably, the hydrocarbon-containing off-gas stream comprises over 5%, e.g., over 15%, such as over 30%, preferably over 40%, hydrocarbons. The concentration of hydrocarbons in this stream is determined prior to any steam addition (i.e., determined as "dry concentration"). A number of recycle streams may be added to various points of the synthesis gas stage—there may either be mixed or added separately—in other words this fourth feed may be several separate or mixed streams.

Yet another possibility is a so-called tail gas from a Fisher-Tropsch unit. This tail gas typically comprises $CO_2$, CO, $H_2$, methane and olefins.

A few examples (not exhaustive) of possible sources of fourth feeds and corresponding synthesis stages are provided in the following table.

| Synthesis stage technology | Possible source of fourth feed from synthesis stage |
| --- | --- |
| Fischer-Tropsch (F-T) | Tail gas |
| | Propane/butane rich stream (LPG) |
| | Naphtha rich stream |
| Methanol (MeOH) synthesis | Purge gas |
| MeOH to gasoline (MTG) | Purge gas |
| | Propane/butane rich stream (LPG) |
| Higher alcohol synthesis (HA) | Tail gas |
| | Methane rich stream |
| Syngas-to-Olefin (STO) synthesis | $CO_2$-rich off gas |
| | Hydrocarbon rich stream |

In some cases, a stream comprising hydrocarbons may be subjected to prereforming before being provided to the syngas stage as the fourth feed. For example, when the fourth feed is e.g., a LPG and/or a naphtha product stream or a natural gas feed, the plant may further comprise a pre-reforming section, arranged in the fourth feed, upstream the syngas stage. A steam feed is arranged to be mixed with the LPG and/or a naphtha product stream, prior to being fed to said pre-reforming section.

In a prereforming step, the following (endothermic) steam reforming reaction and reaction (3) (exothermic) take place to convert higher hydrocarbons. Additional water gas shift and methanation takes place through reactions (1) and (3):

$$C_nH_m + nH_2O \leftrightarrow nCO + (n+m/2)H_2 \text{ (where } n \geq 2, m \geq 4\text{)}. \quad (2)$$

$$CO_2 + 4H_2 \leftrightarrow CH_4 + 2H_2O \quad (3)$$

The prereformer outlet stream will comprise $CO_2$, $CH_4$, $H_2O$, and $H_2$ along with typically lower quantities of CO and possible other components. The prereforming step typically takes place at 350-600° C. or more preferably between 400 and 550° C. Steam is added to the stream comprising hydrocarbons upstream the prereforming step. The prereforming step may take place either adiabatically or in a heated reactor, filled with catalysts including but not limited to Ni-based catalysts. Heating can be achieved by means of hot gas (e.g., ATR effluent gas) or in a heating section for example using a fired heater. Hydrogen or other combustible components may be used to obtain the necessary heat input.

A hydrocarbon-containing off-gas stream may also contain olefins. In this case the olefins may be subjected to hydrogenation to the corresponding paraffins before addition to a prereformer or the syngas stage.

In some cases, the hydrocarbon-containing off-gas stream contains minor amount of poisons, such as sulfur. In this case, the hydrocarbon-containing off-gas stream may be subjected to the step or steps of purification such as desulfurization.

In one aspect, the plant further comprises a steam feed to the syngas stage.

Syngas Stage

The syngas stage is arranged to provide a syngas stream (from at least said first, second third feeds) and feed said syngas stream to the synthesis stage. For the avoidance of doubt, the terms "syngas" and "synthesis gas" are synonymous. Furthermore, the term "provide a syngas stream" in this context must be understood as to "produce a syngas stream".

The syngas stage comprises a methanation section and/or a reverse water gas shift (rWGS) section and an autothermal reforming (ATR) section.

In one embodiment, the methanation section and/or reverse water gas shift (rWGS) section are arranged upstream the autothermal reforming (ATR) section. In another embodiment, the methanation section and/or reverse water gas shift (rWGS) section are arranged in parallel to said ATR section.

The syngas stage may comprise additional sections as required. Various sections will be described in the following.

ATR Section

The syngas stage comprises an autothermal reforming (ATR) section. The ATR section may comprise one or more autothermal reactors (ATR). The key part of the ATR section is the ATR reactor. All feeds are preheated as required. The ATR reactor typically comprises a burner, a combustion chamber, and a catalyst bed contained within a refractory lined pressure shell. In an ATR reactor, partial combustion of the hydrocarbon containing feed by sub-stoichiometric amounts of oxygen is followed by steam reforming of the partially combusted hydrocarbon feed stream in a fixed bed of steam reforming catalyst. Steam reforming also takes place to some extent in the combustion chamber due to the high temperature. The steam reforming reaction is accompanied by the water gas shift reaction. Typically, the gas is at or close to equilibrium at the outlet of the reactor with respect to steam reforming and water gas shift reactions. More details of ATR and a full description can be found in the art such as "Studies in Surface Science and Catalysis, Vol. 152," Synthesis gas production for FT synthesis"; Chapter 4, p. 258-352, 2004".

Typically, the effluent gas from the ATR reactor has a temperature of 900-1100° C. The effluent gas normally comprises $H_2$, CO, $CO_2$, and steam. Other components such as methane, nitrogen, and argon may also be present often in minor amounts. The operating pressure of the ATR reactor will be between 5 and 100 bars or more preferably between 15 and 60 bars.

The syngas stream from the ATR is cooled in a cooling train normally comprising a waste heat boiler(s) (WHB) and one or more additional heat exchangers. The cooling medium in the WHB is (boiler feed) water which is evaporated to steam. The syngas stream is further cooled to below the dew point for example by preheating the utilities and/or partial preheating of one or more feed streams and cooling in air cooler and/or water cooler. Condensed $H_2O$ is taken out as process condensate in a separator to provide a syngas stream with low $H_2O$ content, which is sent to the synthesis stage.

The "ATR section" may be a partial oxidation "POX" section. A POX section is similar to an ATR section except for the fact that the ATR reactor is replaced by a PDX reactor. The POX rector generally comprises a burner and a combustion chamber contained in a refractory lined pressure shell. The ATR section could also be a catalytic partial oxidation (cPOX) section.

Methanation Section

In one aspect, the syngas stage comprises or consists of a methanation section, which is preferably arranged upstream the ATR section. The methanation section is in fluid connection with said ATR section. A part or all of the first feed may be fed to the methanation section; and a part or all of the second feed may be fed to the methanation section.

The heat generated in the methanation process obviates completely or reduces significantly the need for external preheating of the feed to the autothermal reforming section. Such external preheating may for example take place in a fired heater. The required heat in such a fired heater is generated by combustion of for example hydrogen and/or a hydrocarbon. In the former case this consumes part of the feed and in the second case this leads to $CO_2$ emissions. Furthermore, a fired heater is an expensive piece of equipment which may also take up a considerable plot area. Finally, the methanation section upfront the ATR section improves the overall plant efficiency for example compared to a stand-alone ATR section.

As indicated earlier, state of art for producing a synthesis gas from $CO_2$ and hydrogen is based on selective RWGS. Compared to this scheme, the combination of methanation and ATR has several advantages. This includes the possibility of utilizing internal recycle streams. Furthermore, the outlet temperature from the ATR reactor in the ATR section will typically be in the range of 900-1100° C. This is in most cases higher than is possible with a stand-alone RWGS unit. This increases the production of carbon monoxide as this is thermodynamically favoured by higher temperatures. It should also be noted that even if methane is formed in the methanation section, the content of methane in the final synthesis gas sent to the synthesis stage is low due to the high exit temperature from the ATR reaction in the ATR section. Advantageously, the exit temperature from the ATR is between 1000-1100° C.

It is an advantage for most applications that the content of methane in the synthesis gas sent to the synthesis stage is low. For most types of synthesis stages, methane is an inert or even a synthesis stage by-product. Hence, in one preferred embodiment, the content of methane in the synthesis gas sent to the synthesis stage is less than 5%, such as less than 3% or even less than 2%.

It seems counterintuitive to insert a methanation section upstream an ATR section. In the methanation section methane is formed and a large part of the formed methane is then converted in the ATR section. However, the inventors have found that the heat of methanation can be utilized for preheating the feed to the ATR section. This avoids or reduces the need for a dedicated feed preheater. Reducing the preheat duty will also reduce the required combustion to provide the required energy and thereby the emissions of $CO_2$ in case the preheater is a fired heater with hydrocarbon fuel. The methanation section may comprise one or more methanation units, arranged in series, such as two or more methanation units, three or more methanation units or four or more methanation units. In such methanation units, $CO_2$ and $H_2$ are primarily converted to methane and steam via an exothermic methanation reaction. Each of the methanation units may be either adiabatic or cooled by means for example of boiling water or by heating for example the feed gas. The effluent temperature from each methanation unit can be 250-900° C., preferably 600-850° C., more preferably 650-840° C., depending on the extent of methanation and extent of cooling. Parallel methanation units are also conceivable.

In some cases, it may be desirable to avoid to too high temperatures in the methanation unit for example to limit the extent of deactivation of the catalyst due to sintering. This is especially the case if the methanation unit or methanation reactor is adiabatic. The highest temperature in an adiabatic methanation unit will normally be at the outlet. Hence, it may be desirable to control the exit temperature from one or more methanation units to for example a temperature in the range 600-750° C., such as about 650° C., 675° C., 700° C., or 725° C. This may be accomplished by controlling the feed streams to the individual methanation units in the methanation section, if more than one methanation unit is present. By controlling the molar ratios between the part of the first feed and the part of the second feed as well as the molar ratio between the part of the first feed and the part of the fifth feed (if present) added to a methanation unit, it is possible to control the exit temperature of an adiabatic methanation unit. Obviously, the inlet temperature(s) of the feed streams can also be used for this purpose.

The control of the ratios of the various feed streams to the methanation units and the ratios of the various feed streams fed to the methanation section and directly to the methanation section may also be used to impact the synthesis gas composition.

Parts of the first feed comprising hydrogen may be fed separately to different methanation units in the methanation section; or the entire first feed comprising hydrogen may be fed together to the methanation unit located furthest upstream in the methanation section. Similarly, parts of the second feed comprising carbon dioxide may be fed separately to different methanation units in the methanation section; or the entire second feed comprising carbon dioxide may be fed together to the methanation unit located furthest upstream in the methanation section.

In a specific embodiment, all of the first feed comprising hydrogen is fed to the first of the methanation units together with part of the second feed comprising carbon dioxide. The remaining part of the carbon dioxide is distributed between the remaining methanation units and the exit temperature of the final methanation unit is between 650-900° C. such as between 750-850° C.

Additional $H_2$ feed and/or $CO_2$ feed can be added to different parts of the methanation section. For instance, part of the hydrogen or $CO_2$ feed could be provided to a second (or even third . . . ) methanation unit. Additionally, part of the effluent from one methanation unit can be cooled and recycled to the inlet of said methanation unit and/or to the inlet of any additional methanation unit(s) located upstream said one methanation unit. Optionally, effluent from methanation section can be cooled below its dew point and a part of the water may be removed from this effluent before it is recycled to the inlet of the methanation unit or any upstream methanation unit.

A stream comprising $H_2$ and/or $CO_2$ may also be recovered from downstream the ATR section and be recycled to the methanation section.

Addition of steam to the methanation section and/or between the methanation section and the ATR section may also occur.

In this aspect, the exothermic nature of the methanation reaction may be utilized for preheating the ATR feed. Some heating of the ATR section by external means may be either needed or desirable, for example for control purposes. Therefore, the reaction heat of the methanation reaction may only cause part of the temperature increase upstream the ATR section.

The methanation reaction can be expressed by:

$$CO_2 + 4H_2 \leftrightarrow CH_4 + 2H_2O \qquad (3)$$

Normally, the rWGS (reaction (1)) and/or the water gas shift reaction (reverse of reaction (1))) will also take place in the methanation unit. In many cases, the gas composition at the exit of each methanation unit will be at or close to chemical equilibrium with respect to the water gas shift/reverse water gas shift and the methanation reactions at the exit temperature and pressure of said methanation unit.

The methanation reaction (3) is very exothermic. In some cases, it is desirable to adjust the temperature at the outlet of a methanation unit or from the methanation section to a given value which may be in the range of 550-800° C. such as between 600-700° C. If part or all of a fourth feed comprising hydrocarbons is added to a methanation unit, this may reduce the exit temperature due to the fact that steam reforming (reverse of reaction (3) and/or reaction (2)) will take place.

If the effluent from a prereforming step is added to a methanation unit, the exit temperature from such methanation unit will typically be lower than if no such stream is added. The methane in the prereforming step effluent will react according to the endothermic steam reforming reaction:

$$CH_4 + H_2O \leftrightarrow CO + 3H_2 \qquad (4)$$

The presence of methane in the feed will limit the extent of the methanation reaction due to the chemical equilibrium.

The output from the methanation section is a stream comprising $CO_2$, $H_2$, $CO$, $H_2O$ and $CH_4$.

A tail gas from an FT synthesis stage will normally not be added to a methanation unit but fed directly to the ATR section. If excess tail gas from the FT synthesis stage is available, this may be hydrogenated and fed to the methanation section.

In one embodiment, the inlet temperature of at least one of the methanation units will be between 300-500 C.

The control of the ratios of the various feed streams to the methanation units and the ratios of the various feed streams fed to the methanation section and directly to the methanation section may also be used to impact the synthesis gas composition.

The extent of methanation (and thereby the composition of the gas to the ATR section) depends on a number of factors including the ratio of the feed streams to the methanation section and the inlet and exit temperature to and from each methanation unit and the extent of water removal (if any) from the methanation section. For a given gas composition and temperature of the gas to the ATR section, the synthesis gas from the ATR depends upon the amount of oxygen added. Increasing the amount of oxygen increases the ATR reactor exit temperature and thereby reduces the H2/CO-ratio.

In another embodiment (illustrated in FIG. 2c) the syngas stage (A) comprises a methanation section (II) arranged in parallel to said ATR section (I). At least a portion of the first feed and at least a portion of the second feed are arranged to be fed to the methanation section (II) and said methanation section (II) is arranged to convert said at least a portion of the first feed and at least a portion of the second feed to a first syngas stream. A third feed of oxygen is arranged to be fed to the ATR section (I); and wherein said ATR section (I) is arranged to convert part or all of the internally recycled hydrocarbon streams and said third feed comprising oxygen—along with the remaining portions of the first and second streams—to a second syngas stream. The first syngas stream from the methanation section (II) is arranged to be combined with the second syngas stream from the ATR section (I); and the combined syngas stream is arranged to be fed to the synthesis stage (B).

Compared to in series methanation and ATR section, this embodiment reduces the amount of oxygen needed.

Reverse Water Gas Shift (rWGS) Section

In a further aspect, the syngas stage comprises or consists of a reverse water gas shift (rWGS) section, which is preferably arranged upstream the ATR section. The reverse water gas shift (rWGS) section is in fluid connection with said ATR section. A part or all of the first feed is fed to the rWGS section; and a part or all of the second feed is fed to the rWGS section.

As indicated earlier, state of art for producing a synthesis gas from $CO_2$ and hydrogen is based on selective RWGS. Compared to this scheme, the combination of RWGS and ATR has several advantages. This includes the possibility of utilizing internal recycle streams. Such streams can be added to the ATR section and utilized for additional synthesis gas production compared to what is possible with a stand-alone and selective RWGS. Furthermore, the outlet temperature from the ATR reactor in the ATR section will typically be in the range of 900-1100° C. This is in most cases higher than is possible with a stand-alone RWGS unit. This increases the production of carbon monoxide as this is thermodynamically favoured by higher temperature.

In one aspect, the rWGS section comprises one or more rWHS units, arranged in series e.g., two or more rWGS units, such as three or more rWGS units. In such rWGS units, $CO_2$ and $H_2$ are converted to CO and $H_2$ via reaction (1) above. Parallel reverse water gas shift units are also conceivable.

Parts of the first feed comprising hydrogen may be fed separately to different rWGS units in the rWGS section; or the entire first feed comprising hydrogen is fed together to the reverse WGS unit located furthest upstream in the rWGS section. Similarly, parts of the second feed comprising carbon dioxide may be fed separately to different rWGS units in the rWGS section; or the entire second feed comprising carbon dioxide is fed all together to the rWGS unit located furthest upstream in the rWGS section.

Each of the rWGS units may be either adiabatic or a heated reactor. Heating can be achieved by means of hot effluent from ATR or utilizing heat of combustion of for example a stream comprising hydrocarbons and/or a stream comprising hydrogen. The effluent from the rWGS section is a stream comprising $CO_2$, $H_2$, CO, $H_2O$. The rWGS effluent temperature from each rWGS unit can be 400-900° C., preferably 500-900° C., more preferably 500-750° C., depending on the extent of rWGS and extent of heating.

The effluent from the rWGS section is fed to the ATR section. A methanation section, in one specific embodiment, may be placed between the rWGS section and the ATR section. In this case the effluent from the rWGS section is fed to the methanation section and the effluent from the methanation section is fed to the ATR.

Reverse Water Gas Shift (rWGS) Section—Alternative Arrangement

In a further aspect, the syngas stage comprises a reverse water gas shift (rWGS) section which is arranged in parallel to said ATR section. The reverse water gas shift (rWGS) section is in fluid connection with said ATR section. A part or all of the first feed is fed to the rWGS section; a part or all of the second feed is fed to the rWGS section; wherein the said rWGS section is arranged to convert at least a portion of the first feed and at least a portion of the second feed to a syngas stream comprising $H_2$, CO, $CO_2$ and $H_2O$.

Third feed comprising oxygen along with optionally a portion of first feed comprising hydrogen and/or optionally a portion of second feed comprising carbon dioxide are arranged to feed to ATR section; wherein the said ATR section is arranged to convert the feed streams to another syngas stream comprising $H_2$, CO, $CO_2$, $CH_4$ and $H_2O$ The third feed comprising oxygen and the fourth feed of hydrocarbons are also added to this ATR section.

In this aspect, syngas streams from the rWGS section and the ATR section are arranged to be combined to obtain a final syngas stream; wherein the said final syngas stream is fed to synthesis stage.

As indicated earlier, state of art for producing a synthesis gas from $CO_2$ and hydrogen is based on selective RWGS. Compared to this scheme, the combination of a parallel RWGS and ATR has several advantages. This includes the possibility of utilizing internal recycle streams. Converting part of the $CO_2$ in the RWGS section has the advantage that the overall oxygen consumption may be reduced.

As above, this rWGS section may comprise one or more rWGS units, arranged in series e.g., two or more rWGS units, such as three or more rWGS units. In such rWGS units, $CO_2$ and $H_2$ are converted to CO and $H_2$ via reaction (1) above. Parallel reverse water gas shift units are also conceivable.

Parts of the first feed comprising hydrogen may be fed separately to different rWGS units in the rWGS section; or the entire first feed comprising hydrogen is fed together to the reverse WGS unit located furthest upstream in the rWGS section. Similarly, parts of the second feed comprising carbon dioxide may be fed separately to different rWGS units in the rWGS section; or the entire second feed comprising carbon dioxide is fed all together to the rWGS unit located furthest upstream in the rWGS section.

Each of the rWGS units may be either adiabatic or a heated reactor. Heating can be achieved by means of hot effluent from ATR or utilizing heat of combustion of, for example—a stream comprising hydrocarbons and/or a stream comprising hydrogen. The effluent from the rWGS section is a stream comprising $CO_2$, $H_2$, CO, $H_2O$. The rWGS effluent temperature from each rWGS unit can be 400-900° C., preferably 500-900° C., more preferably 500-750° C., depending on the extent of rWGS and extent of heating.

Post ATR $CO_2$-Conversion Unit

In another aspect, the plant comprises a post-conversion (post-ATR conversion, PAC) unit or reactor, located downstream the ATR section.

The PAC unit may be either adiabatic or a heated reactor using for example a Ni-based catalyst and/or a catalyst with noble metals such as Ru, Rh, Pd, and/or Ir as the active material. In such a PAC unit, a stream comprising carbon dioxide such as part of the second feed and part or all of the syngas from the ATR section is mixed and directed to the PAC unit. The mixed stream is converted to a syngas with higher carbon monoxide content via both reactions (3) and (1)—above—in the PAC unit. Reactions (3) and (1) will typically be at or close to chemical equilibrium at the outlet of the PAC unit. The effluent from the PAC section is a stream comprising $CO_2$, $H_2$, CO, $H_2O$ and $CH_4$. The PAC effluent temperature from each PAC unit can be 700-1000° C., preferably 800-950° C., more preferably 850-920° C. The advantage of the PAC unit is the ability to produce a synthesis gas a lower $H_2$/CO-ratio compared to the effluent stream from the ATR section. Furthermore, the fact that a stream comprising carbon dioxide such as part of the second feed is directed to the PAC unit (such as an adiabatic PAC unit) instead of to the ATR section, reduces the size of the ATR section. This may in some cases reduce the overall cost.

The effluent stream from the PAC unit is cooled as described above to provide a syngas stream for the synthesis stage.

This $CO_2$-conversion (PAC) unit may be included in any of the aspects described above.

Synthesis Stage

The synthesis stage is typically arranged to convert the syngas stream into at least a product stream. Often a hydrocarbon-containing off-gas stream is generated in the synthesis stage. Suitably, at least a portion of said hydrocarbon-containing off-gas stream is fed to the syngas stage as a fourth feed, upstream of said ATR section and preferably between said methanation section and/or reverse water gas shift (rWGS) section, and said ATR section.

As noted, the plant does not comprise an external hydrocarbon feed such as natural gas feed. Therefore, the only source of carbon fed to the syngas stage comes from the second feed of carbon dioxide and recycle stream(s) from the synthesis stage.

The syngas stream at the inlet of said synthesis stage suitably has a $H_2$:CO ratio in the range 1.00-4.00; preferably 1.50-3.00, more preferably 1.50-2.10. If the synthesis stage is an FT stage, the $H_2$:CO ratio is preferably in the range 1.50-2.10.

In another embodiment, the syngas stream at the inlet of said synthesis stage suitably has a $(H_2-CO_2)/(CO+CO_2)$ ratio in the range 1.50-2.50; preferably 1.80-2.30, more preferably 1.90-2.20.

A few potential examples of the synthesis stage are provided in the following.

Fischer-Tropsch Synthesis Stage

In one aspect, the synthesis stage is a Fischer-Tropsch synthesis (F-T) stage. The F-T stage comprises Fischer-Tropsch (F-T) synthesis section where syngas from syngas stage is first converted to at least a raw product comprising hydrocarbons and a hydrocarbon containing off-gas stream in form of an F-T tail gas stream followed by hydroprocessing and hydrocracking section where said raw product is converted to at least one or more hydrocarbon product streams. The ratio between long chain hydrocarbons and olefins in the raw product from the F-T synthesis section depends on the type of catalyst, reaction temperature etc. that are used in the process.

A hydrocarbon-containing off-gas stream in the form of an F-T tail gas stream is produced as side product. The F-T tail gas stream typically comprises carbon monoxide (10-40 vol. %), hydrogen (10-40 vol %), carbon dioxide (10-50 vol %), and methane (10-40 vol %). Additional components such as argon, nitrogen, olefins, and paraffins with two or more carbon atoms may also be present in smaller amounts.

At least a portion of said F-T tail gas stream may be fed to the syngas stage as said fourth feed comprising hydrocarbons. Suitably, to avoid excessive build-up of inert components, that may be present in F-T tail gas, only a portion of said F-T tail gas stream is fed to the syngas stage as said fourth feed; and another portion of the F-T tail gas may be purged and/or used as fuel and/or converted to power. In one embodiment said power can be used as (partial) source for an electrolysis unit if present. Alternatively, the power can be exported. Note that F-T tail gas will typically be fed between the methanation section and the ATR section.

In one embodiment, the major product from F-T synthesis stage is/are typically jet fuel and/or kerosene (e.g., comprising primarily $C_{12}$-$C_{15}$) and/or diesel (e.g., comprising primarily $C_{15}$-$C_{20}$). Besides, naphtha (e.g., comprising primarily $C_5$-$C_{12}$) and LPG (e.g., comprising primarily $C_3$-$C_4$) streams are also produced in F-T synthesis stage. A part or all of such LPG and/or naphtha stream(s) from F-T synthesis stage may also be used as said fourth feed comprising hydrocarbons. A part or all of such LPG and/or naphtha stream(s) may be added to the methanation section and/or directly to the ATR section. In another embodiment, a part or all of such LPG and/or naphtha may be subjected to prereforming section before addition to the methanation section and/or the ATR section.

In one particular embodiment, therefore, the synthesis stage is a Fischer-Tropsch (F-T) stage arranged to convert said syngas stream into at least a hydrocarbon product stream, being a diesel stream; and an LPG and/or a naphtha product stream and/or kerosene or jet fuel product stream, and wherein at least a portion of said diesel stream; and LPG and/or a naphtha product stream and/or kerosene or jet fuel product stream is fed to the syngas stage. In one aspect, at least a portion of the FT tail gas, at least a portion of the LPG and at least a portion of the naphtha product stream are fed to the syngas stage. In another aspect, at least a portion of the FT tail gas and at least a portion of the LPG are fed to the syngas stage. The LPG and/or naphtha stream(s) may be treated by prereforming before being fed to the syngas stage.

Note that the term "FT stage" in the present context may include further process steps such as hydroprocessing of the raw effluent from the FT reactor.

Methanol Synthesis Stage

In another embodiment, the synthesis stage is a methanol (MeOH) synthesis stage. This stage comprises a MeOH synthesis section where syngas from the syngas stage is first converted to a raw MeOH stream, followed by a purification section where said raw MeOH stream is purified to obtain a MeOH product stream. The MeOH synthesis stage generates a purge gas stream, which typically contains hydrogen, carbon dioxide, carbon monoxide and methane. Additional components such as argon, nitrogen, or oxygenates with two or more carbon atoms may also be present in smaller amounts.

At least a portion of said MeOH purge gas stream may be fed to the syngas stage as said fourth feed comprising hydrocarbons. The MeOH purge gas stream may be purified prior to feeding it to the syngas stage. Suitably, to avoid excessive build-up of inert components that may be present in the MeOH purge gas, only a portion of said MeOH purge gas stream may be fed to the syngas stage; and another portion of the MeOH purge gas may be purged and/or used as fuel.

In particular when the synthesis stage is a methanol synthesis stage, the syngas stream at the outlet of said syngas stage has a module, as defined herein, in the range 1.80-2.30; preferably 1.90-2.20. The term "module" is defined as:

$$\text{Module}, M = \frac{(H_2 - CO_2)}{(CO + CO_2)}$$

Methanol-to-Gasoline (MTG) Synthesis Stage

In another embodiment, the synthesis stage is a MeOH-to-gasoline (MTG) synthesis stage comprising a MeOH synthesis section where syngas from syngas stage is first converted to raw MeOH stream followed by a gasoline synthesis section where said raw MeOH stream is converted to gasoline product stream.

The MTG synthesis stage also generates a purge gas stream. This purge gas stream can be utilized similarly as explained in the previous section under 'Methanol synthesis stage'.

The MTG synthesis stage generates LPG (e.g., comprising primarily $C_3$-$C_4$) stream. A part or all of such LPG stream from MTG synthesis stage may also be fed as said fourth feed comprising hydrocarbons to the synthesis stage. A part or this entire LPG stream may be added to the methanation section and/or directly to the ATR section. In another embodiment, a part or all of said LPG stream may be subjected to prereforming before addition to the methanation section and/or the ATR section.

Higher Alcohol (HA) Synthesis

In another embodiment, the synthesis stage is a higher alcohol (HA) synthesis stage comprising HA synthesis section where syngas from syngas stage is first converted to raw alcohol stream followed by purification section where said raw alcohol stream is purified to get HA product stream.

HA synthesis stage may generate a tail gas stream, which typically contains hydrogen, carbon dioxide, carbon monoxide. Additional components such as argon, nitrogen, methane, oxygenates with two or more carbon atoms may also be present in smaller amounts.

HA synthesis stage may also generate a methane rich stream, which typically contains methane, hydrogen and carbon monoxide. Additional components such as argon, nitrogen, carbon dioxide, oxygenates with two or more carbon atoms may also be present in smaller amounts.

At least a portion of said tail gas and/or said methane rich stream(s) may be fed to the syngas stage. Suitably, to avoid excessive build-up of inert components, that may be present in said tail gas and/or said methane rich stream(s), only a portion of said tail gas and/or said methane rich stream(s) may be fed to the syngas stage as said fourth feed; and the another portion may be purged and/or used as fuel.

Syngas-to-Olefins (STO) Synthesis

In another embodiment, the synthesis stage is a syngas-to-olefins (STO) synthesis stage comprising STO synthesis section where syngas from syngas stage is first converted to raw olefin rich stream followed by purification section where said raw olefin rich stream is purified to get olefin product stream.

STO synthesis stage may generate a tail gas stream, which typically contains hydrogen, carbon dioxide, carbon monoxide. Additional components such as argon, nitrogen, methane, hydrocarbons with two or more carbon atoms may also be present in smaller amounts.

STO synthesis stage may also generate a hydrocarbon rich stream, which typically contains methane and higher hydrocarbons with two or more carbon atoms. Higher hydrocarbons may be both olefins and paraffins. Additional components such as hydrogen, carbon dioxide, carbon monoxide, argon, nitrogen may also be present in smaller amounts.

At least a portion of said tail gas and/or said hydrocarbon rich stream(s) may be fed to the syngas stage. Suitably, to avoid excessive build-up of inert components, that may be present in said tail gas and/or said hydrocarbon rich stream(s), only a portion of said tail gas and/or said hydrocarbon rich stream(s) may be fed to the syngas stage as said fourth feed; and the another portion may be purged and/or used as fuel.

Syngas-to-Ethylene Oxide (STEtO) Synthesis

In another embodiment, the synthesis stage is a syngas-to-ethylene oxide (STEtO) synthesis stage. The STEtO stage comprises syngas-to-olefin (STO) synthesis section, where syngas is first converted to olefin product (mainly ethylene), followed by the ethylene oxide synthesis section.

STO synthesis stage may generate a tail gas stream, which typically contains hydrogen, carbon dioxide, carbon monoxide. Additional components such as argon, nitrogen, methane, hydrocarbons with two or more carbon atoms may also be present in smaller amounts.

STO synthesis stage may also generate a hydrocarbon rich stream, which typically contains methane and higher hydrocarbons with two or more carbon atoms. Higher hydrocarbons may be both olefins and paraffins. Additional components such as hydrogen, carbon dioxide, carbon monoxide, argon, nitrogen may also be present in smaller amounts.

At least a portion of said tail gas and/or said hydrocarbon rich stream(s) may be fed to the syngas stage. Suitably, to avoid excessive build-up of inert components, that may be present in said tail gas and/or said hydrocarbon rich stream(s), only a portion of said tail gas and/or said hydrocarbon rich stream(s) may be fed to the syngas stage; and the another portion may be purged and/or used as fuel.

The ethylene oxide synthesis section may use at least a part of the fourth feed ($O_2$). Lots of $CO_2$ is generated as by-product during ethylene oxide synthesis. The $CO_2$ by-product can be recycled and used at least a part of the first feed to the syngas stage.

Combined Gasoline and Diesel Production

In another embodiment, the synthesis stage can be a combination of an F-T section and methanol-to-gasoline (MTG) synthesis sections in parallel with a common syngas feed from the syngas stage. The F-T section produces middle distillate products (diesel/jet fuel/kerosene etc.), and MTG produces gasoline with a desired octane number. In this embodiment, the syngas stage provides syngas of suitable quality to both F-T and MTG sections, operating in parallel to each other. At least a part of recycle gas from F-T and/or at least a part of LPG stream from MTG section and/or at least a part of purge stream from MeOH synthesis section can be used as fourth feed to syngas stage.

Electrolyser

The plant may further comprise an electrolyser arranged to convert water or steam into at least a hydrogen-containing stream and an oxygen-containing stream, wherein at least a part of said hydrogen-containing stream from the electrolyser is fed to the syngas stage as said first feed and/or wherein at least a part of said oxygen-containing stream from the electrolyser is fed to the syngas stage as said third feed. An electrolyser s may comprise one or more electrolysis units, for example based on—solid oxide electrolysis.

In one preferred embodiment, therefore, the plant further comprises an electrolyser located upstream the syngas stage. The electrolyser is arranged to convert water or steam into at least a hydrogen-containing stream and an oxygen-containing stream.

At least a part of the hydrogen-containing stream from the electrolyser is fed to the syngas stage as said first feed. Alternatively or additionally, at least a part of the oxygen-containing stream from the electrolyser is fed to the syngas stage as said third feed. This provides an effective source of the first and third feeds.

In a preferred aspect, all of the hydrogen in the first feed and all of the oxygen in the third feed is produced by electrolysis. In this manner the hydrogen and the oxygen required by the plant is produced by steam and electricity. Furthermore, if the electricity is produced only by renewable sources, the hydrogen and oxygen in the first and third feed, respectively, are produced without fossil feedstock or fuel.

Preferably, the water or steam fed to the electrolyser is obtained from one or more units or stages in said plant. The use of an electrolyser may be combined with any of the described embodiments in this document.

Additional Aspects

Optionally, the plant may comprise a sixth feed comprising hydrogen to the syngas stream, upstream the synthesis stage. This sixth feed may have the same composition as the first feed comprising hydrogen, i.e., the sixth feed consists essentially of hydrogen, and over 75%, such as over 85%, preferably over 90%, more preferably over 95%, even more preferably over 99% of this feed may be hydrogen.

The sixth feed can be used to adjust the syngas composition (such as the $H_2/CO$ ratio) in the syngas stream, if required. In a preferred aspect, at least a part of the hydrogen-containing stream from an electrolyser is fed to the syngas stream, upstream the synthesis stage as said sixth feed of hydrogen. This provides additional opportunities for a system which does not require additional external input of gas and allows final adjustment of the gas composition upstream the synthesis stage.

The composition of the syngas from the syngas stage can be adjusted in other ways. For instance, the plant may further comprise a hydrogen removal section, located between said syngas stage and said synthesis stage, arranged to remove at least part of the hydrogen from the syngas stream. In this case, at least a portion of the hydrogen removed from the syngas stream in said hydrogen removal section may be compressed and fed as said part of said first feed to the syngas stage. Hydrogen removal units can be, but not limited to, pressure swing adsorption (PSA) units or membrane units.

Furthermore, the plant may further comprise a carbon dioxide removal section, located between said syngas stage and said synthesis stage, and arranged to remove at least part of the carbon dioxide from the syngas stream. In this case, at least a portion of the carbon dioxide removed from the syngas stream in said carbon dioxide removal section may be compressed and fed as said part of said second feed to the syngas stage. Carbon dioxide removal units can be, but not limited to, an amine based unit or a membrane unit.

An off-gas stream may be treated to remove one or more components, or to change the chemical nature of one or more components, prior to being fed to the syngas stage. The off-gas, for example when it is an F-T tail gas, may comprise olefins. Olefins increase the risk of carbon deposition and/or metal dusting at high temperatures. Therefore, the plant may further comprise a hydrogenator arranged in the F-T tail gas recycle stream. The hydrogenator arranged to hydrogenate the fourth feed, before said fourth feed enters the syngas stage. In this manner, olefins can effectively be converted to saturated hydrocarbons before entering the syngas stage.

An off-gas stream or the part of an off-gas stream not recycled to the synthesis gas stage or used for other purposes may be used to produce additional synthesis gas in a separate synthesis gas generator. Such a synthesis gas generator may comprise technologies known in the art such as ATR, steam reforming (SMR), and/or adiabatic prereforming, but also other technologies are known. Such additional synthesis gas may be fed to the synthesis stage. As an example, tail gas from a Fischer-Tropsch synthesis stage may be converted into additional synthesis gas by means known in the art such as comprising hydrogenation, followed by water gas shift, and autothermal reforming.

Method

A method for producing a product stream is provided, said method comprising the steps of:
  providing a plant as defined herein;
  supplying a first feed comprising hydrogen to the syngas stage;
  supplying a second feed comprising carbon dioxide to the syngas stage;
  supplying a third feed comprising oxygen to the ATR section; and
  converting said first, second, third and—optionally, fourth—feeds in said syngas stage to a syngas stream and feeding said syngas stream to the synthesis stage;
  converting said syngas stream in said synthesis stage into at least a product stream and a hydrocarbon-containing off-gas stream; and
  optionally, feeding at least a portion of said hydrocarbon-containing off-gas stream or at least a portion of said product stream to the syngas stage as a fourth feed comprising hydrocarbons, upstream of said ATR section and preferably between the methanation section and/or the reverse water gas shift (rWGS) section and said ATR section.

All aspects relating to the plant set out above are equally applicable to the method using said plant. The term "feed"—when applied to the method of the invention—refers to providing a flow of said gas to the appropriate stage, reactor or unit. In particular, the following aspects of particular importance to the method of the invention are noted:
  convert said syngas stream in said synthesis stage into at least a product stream and, optionally, a hydrocarbon-containing off-gas stream,
  feeding at least a portion of said hydrocarbon-containing off-gas stream to the syngas stage as a fourth feed comprising hydrocarbons, upstream of said ATR section and preferably between said methanation section and/or reverse water gas shift (rWGS) section, and said ATR section,
  the synthesis stage may be a Fischer-Tropsch (F-T) stage arranged to convert said syngas stream into at least a hydrocarbon product stream and a hydrocarbon-containing off-gas stream in the form of an F-T tail gas stream.

an electrolyser may be located upstream the syngas stage and the method may further comprise conversion of water or steam into at least a hydrogen-containing stream and an oxygen-containing stream. The method may further comprise the steps of; feeding at least a part of said hydrogen-containing stream from the electrolyser to the syngas stage as said first feed of hydrogen and/or feeding at least a part of said oxygen-containing stream from the electrolyser to the syngas stage as said fourth feed of oxygen. The method may further comprise obtaining the water or steam which is fed to the electrolyser is obtained as condensate or steam from one or more units or stages in said plant.

DETAILED DESCRIPTION OF THE FIGURES

FIG. 1 illustrates a schematic layout of a first embodiment of a plant:
A syngas stage
B synthesis stage
1 first feed (comprising hydrogen) to syngas stage (A)
2 second feed (comprising carbon dioxide) to syngas stage (A)
3 third feed (comprising oxygen) to syngas stage (A)
100 syngas product from syngas stage (A)
500 product from synthesis stage (B)

FIG. 1a illustrates a schematic layout of a first embodiment of a plant, including recycle of hydrocarbon-containing streams as fourth feed comprising hydrocarbons. Reference numbers are for FIG. 1, plus:
4a a part of fourth feed from synthesis stage (e.g., tail gas from F-T) to syngas stage (A)
4b another part of fourth feed from synthesis stage (e.g., LPG stream from F-T) to syngas stage (A)
4c another part of fourth feed from synthesis stage (e.g., naphtha stream from F-T) to syngas stage (A)

Figure 2:
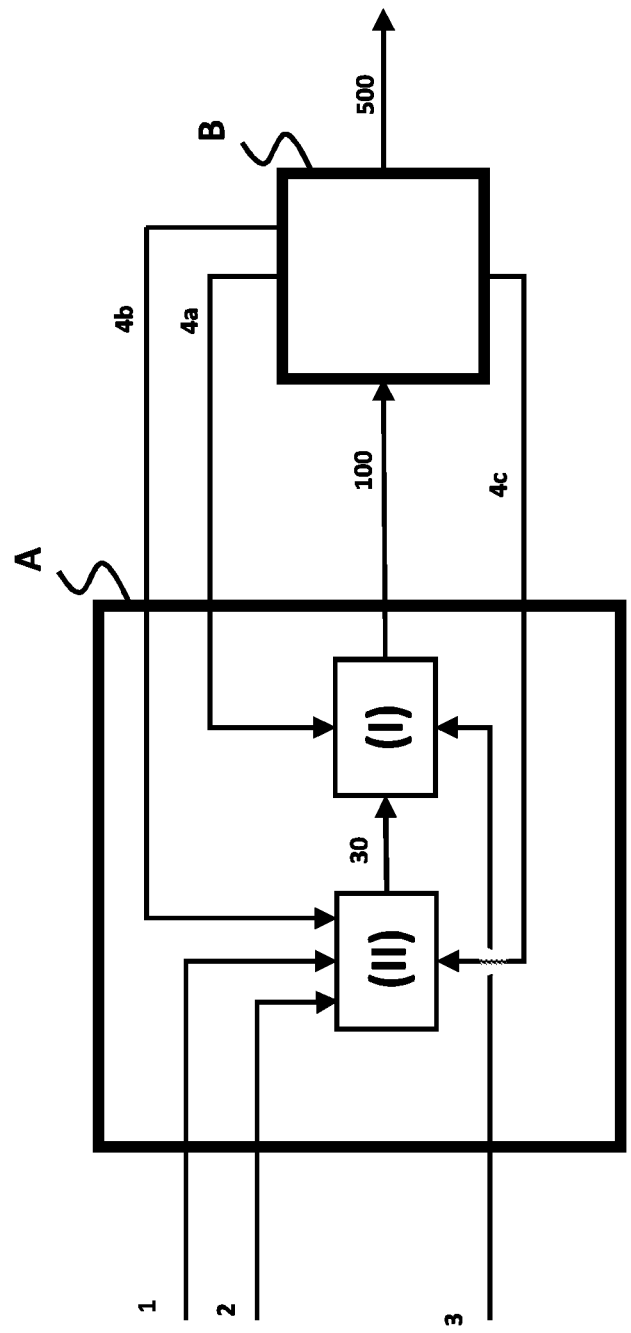

FIG. 2 illustrates a schematic layout of another embodiment of a plant, in which the syngas stage comprises methanation section (II) and ATR section (I). The effluent from methanation section (II) is sent to ATR section (I). Reference numbers are as for the previous figures, plus:
(I) ATR section
(II) methanation section
30 effluent from methanation section (II) to ATR section (I)

Figure 2A:
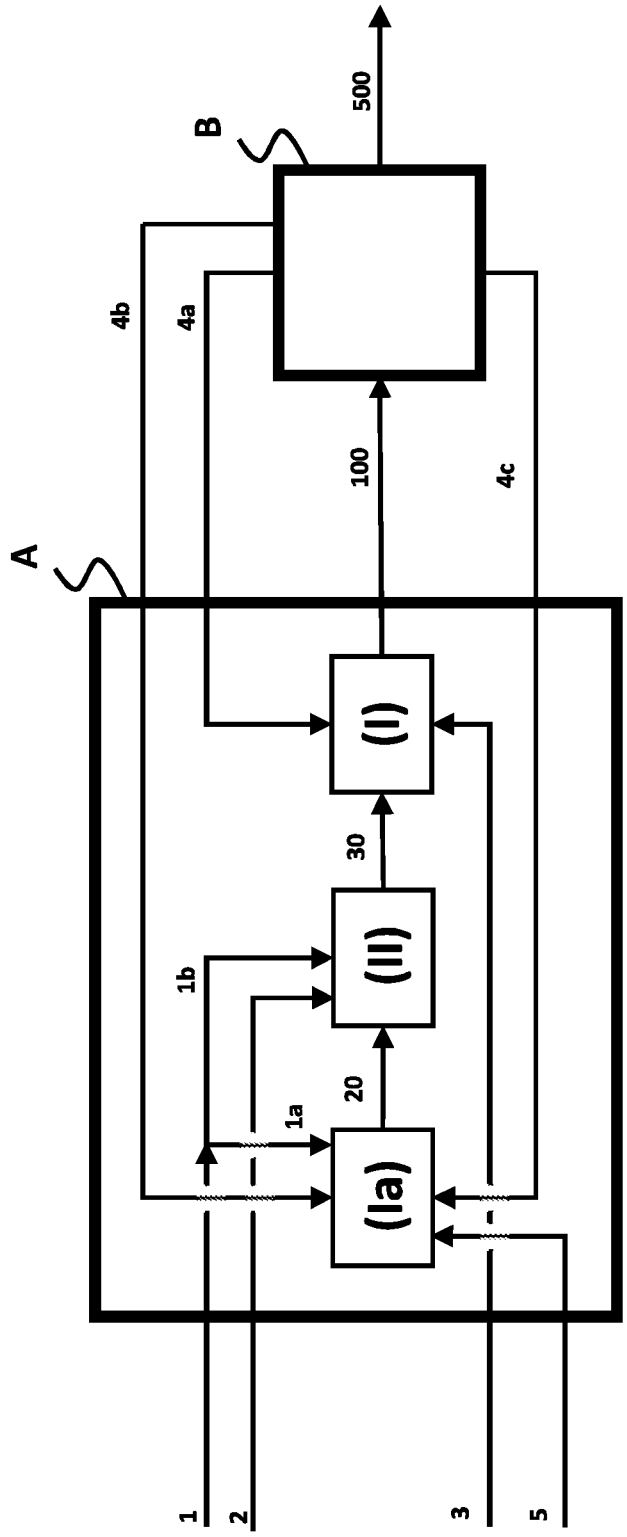

FIG. 2a illustrates a variation of the schematic layout, described in FIG. 2. In this embodiment of a plant, hydrocarbon feeds are treated in prereforming section (Ia) before feeding it to methanation section (II) followed by ATR section (I). Fifth feed steam (5) is introduced to prereforming section. Reference numbers are as for the previous figures, plus:
(Ia) prereforming section
1a part of first feed to prereforming section (Ia)
1b part of first feed to ATR section (I)
20 prereformed hydrocarbon to methanation section (II)
5 fifth feed (steam)

FIG. 2b illustrates a schematic layout of another embodiment of a plant, in which the syngas stage comprises a prereforming section (Ia), methanation section (II) plus ATR section (I) with steam addition (5b) to the methanation section (II) and steam addition (5a) to the prereforming section. The effluent from methanation section (II) is sent to ATR section (I). Reference numbers are as for the previous figures, plus:
5a part of fifth feed to prereforming section (Ia)
5b part of the fifth feed to methanation section (II)

FIG. 2c illustrates a schematic layout of another embodiment of a plant, in which the syngas stage comprises prereforming section (Ia), methanation section (II) and ATR section (I), and where methanation section (II) and ATR section (I) are arranged in parallel. Reference numbers are as for the previous figures, plus:
31 first syngas stream from the methanation section (II)
50 second syngas stream from the ATR section (I)
100 combined syngas stream.

Figure 3:
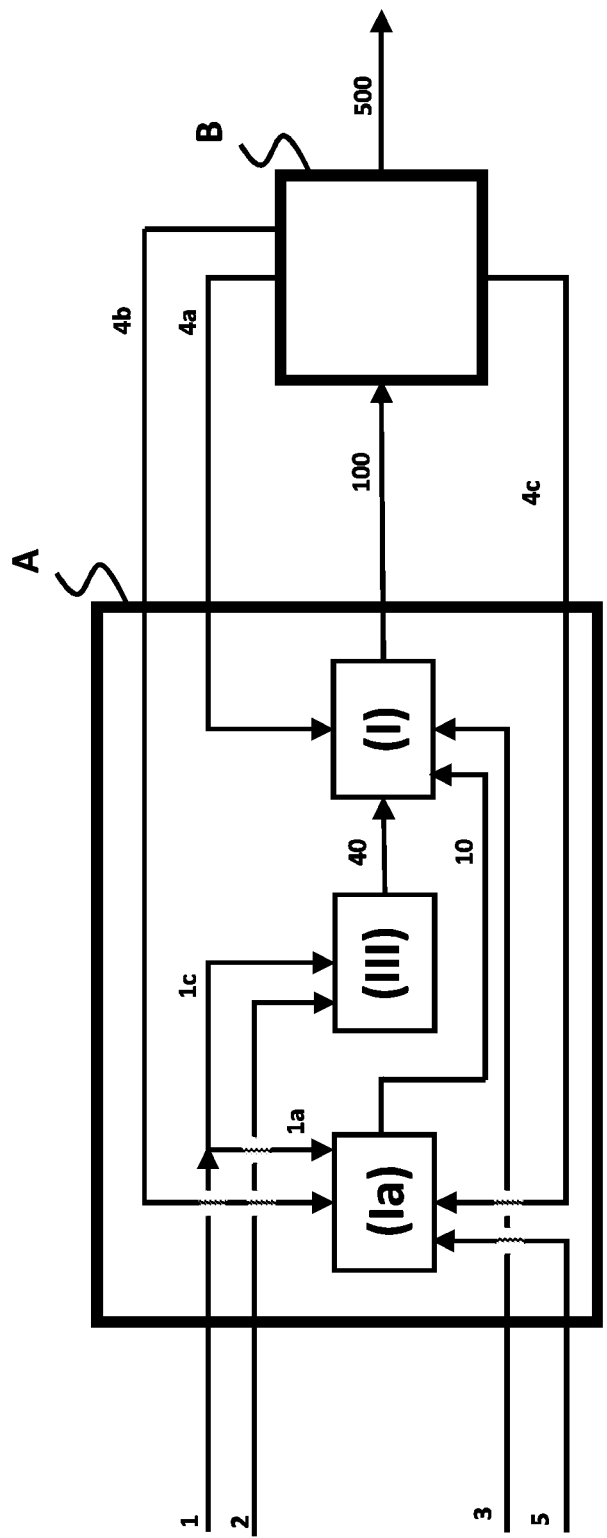

FIG. 3 illustrates a schematic layout of another embodiment of a plant, in which the syngas stage comprises prereforming section (Ia), an rWGS section (III) plus an ATR section (I). Reference numbers are as for the previous figures, plus:
(III) rWGS section
1c part of first feed to section rWGS section (III)
10 preformed hydrocarbon to ATR section (I)
40 effluent from rWGS section (III) to ATR section (I).

Figure 3A:
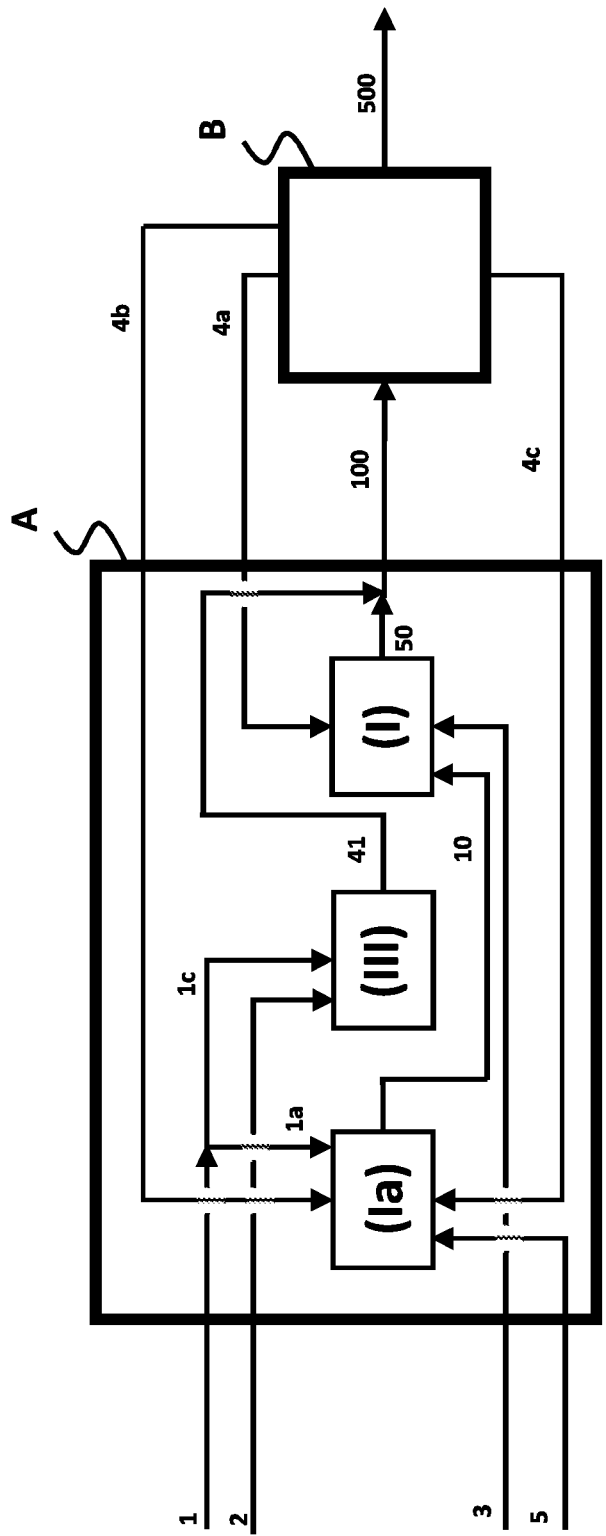

FIG. 3a illustrates a schematic layout of another embodiment of a plant, in which the syngas stage comprises an rWGS section (III) plus an ATR section (I). In this layout, rWGS section (III) and ATR section (I) are parallel to each other. Reference numbers are as for the previous figures, plus:
41 first syngas from rWGS section (III)
50 second syngas stream from ATR section (I)

Figure 3B:
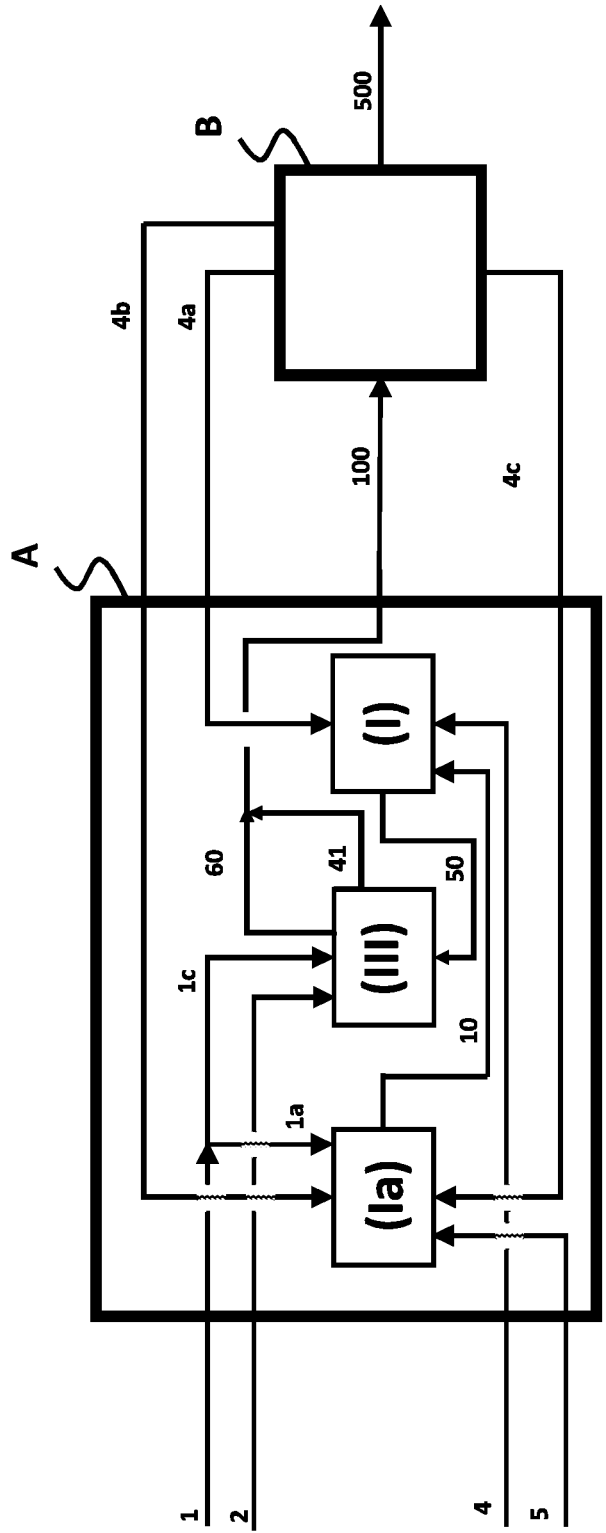

FIG. 3b illustrates a schematic layout of another embodiment of a hydrocarbon plant, as per FIG. 3a. In the layout of FIG. 3b, the syngas stream 50 from the ATR section (I) is arranged to heat the rWGS section (III). Effluent from ATR section (I) gets cooled to become syngas stream 60 by exchanging heat with rWGS section and then is combined with the syngas stream 41 from the rWGS section (III).
60 cooled syngas stream from ATR section (I) after cooling in rWGS section (III)

Figure 4:
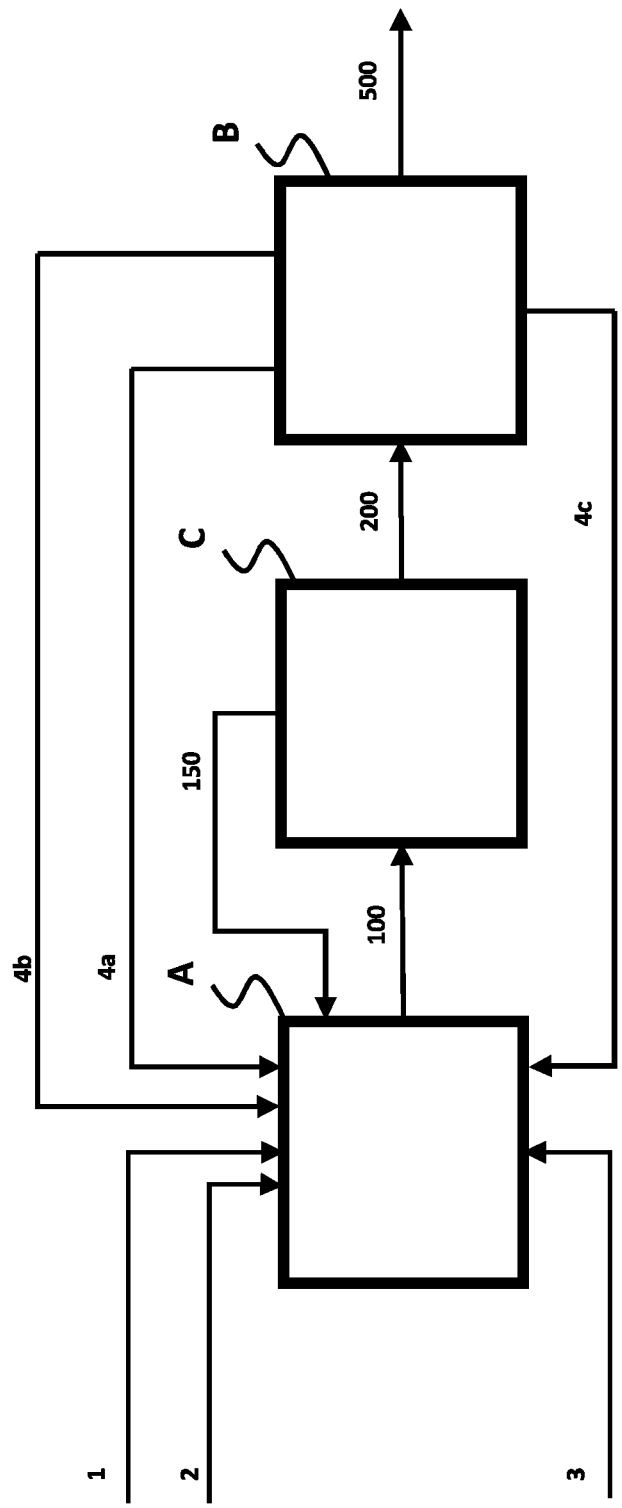

FIG. 4 illustrates a schematic layout of another embodiment of a plant, in which a component recovery stage (C)—i.e. recovery and recycle of either hydrogen or more $CO_2$—is present between the syngas stage (A) and the synthesis stage (B). Reference numbers are as for the previous figures, plus:
C component recovery stage
150 recycle gas from component recovery stage
200 syngas from component recovery stage

EXAMPLES

In this section, the advantages of a novel process for utilization of $CO_2$-rich feed have been quantified and compared with a conventional plant, based on hydrocarbon feed.

In C1, important process parameters from a conventionally designed syngas stage (A), which consumes primarily hydrocarbon feed, is shown. This syngas stage, comprising an autothermal reformer (ATR) section (I), provides syngas to the synthesis stage (B) for production of liquid fuels via Fischer-Tropsch (FT) synthesis. In this example, utilization of $CO_2$ in a conventional syngas stage has been maximized without compromising the integrity of existing equipment. However, utilization of internal recycle of the hydrocarbon stream from the synthesis stage (B) becomes compromised.

In C2-C4, $CO_2$ rich feed (2) with a $H_2$ rich feed (1) have been primarily used as feeds. The layout in syngas stage (A) is based on a methanation section (II) followed by ATR section (I). The third feed (3) of oxygen is used in ATR section (I) along with internally recycled hydrocarbon stream from synthesis stage (B) which produces liquid fuels based on Fischer-Tropsch synthesis.

TABLE 1

| Parameters | Unit | C1 | C2 | C3 | C4 |
|---|---|---|---|---|---|
| $H_2$ content in first feed (1) | mol % | 99.0 | 99.0 | 99.0 | 99.0 |
| $CO_2$ content in second feed (2) | mol % | 99.9 | 99.9 | 99.9 | 99.90 |
| First feed (1)/second feed (2) | — | 2.97 | 4.95 | 4.51 | 3.77 |
| External hydrocarbon feed/second feed (2) | — | 1.34 | 0.00 | 0.00 | 0.00 |
| Third feed (3)/first feed (1) | — | 0.38 | 0.14 | 0.15 | 0.16 |
| Steam/first feed (1) | — | 0.31 | 0.03 | 0.03 | 0.04 |
| $H_2/CO$ in syngas product (100) | — | 2.08 | 2.42 | 2.15 | 1.89 |
| CO in syngas product (100)/total C in feeds (both external and internal streams) | % | 74.46 | 80.73 | 80.59 | 77.76 |
| Relative $CO_2$ emission in syngas stage (A)/1000 $Nm^3$ ($H_2$ + CO) product | % | 100 | 0 | 0 | 0 |

In table 1, relative $CO_2$ emission is estimated with respect to $CO_2$ emission in C1 as basis. As it can be seen in C2-C4, no hydrocarbon combustion takes place, causing no CO2 emission from syngas stage (A). Moreover, similar or even better conversion of feed to CO in syngas can be achieved in syngas stage (A) with utilization of $CO_2$ rich feed. The examples also demonstrate that the layout is flexible enough to produce syngas with different $H_2/CO$ ratios suitable for downstream synthesis stage (B).

The following numbered aspects are provided:

Aspect 1. A plant, said plant comprising:
  a. a syngas stage, said syngas stage comprising a methanation section and/or a reverse water gas shift (rWGS) section, and an autothermal reforming (ATR) section; and
  b. a synthesis stage;
said plant comprising:
  a first feed comprising hydrogen to the syngas stage;
  a second feed comprising carbon dioxide to the syngas stage;
  a third feed comprising oxygen to the ATR section;
wherein said syngas stage is arranged to provide a syngas stream and feed said syngas stream to the synthesis stage; and wherein the plant does not comprise an external feed of hydrocarbons.

Aspect 2. The plant according to aspect 1, wherein the syngas stage comprises a methanation section (II) and/or a reverse water gas shift (rWGS) section (III), arranged upstream the autothermal reforming (ATR) section (I).

Aspect 3. The plant according to aspect 1, wherein the syngas stage comprises a methanation section (II) and/or a reverse water gas shift (rWGS) section (III), arranged in parallel to the autothermal reforming (ATR) section (I).

Aspect 4. The plant according to any one of the preceding aspects, wherein the synthesis stage is arranged to convert said syngas stream into at least a product stream and, optionally, a hydrocarbon-containing off-gas stream.

Aspect 5. The plant according to aspect 4, wherein at least a portion of said hydrocarbon-containing off-gas stream or at least a portion of said product stream is fed to the syngas stage as a fourth feed comprising hydrocarbons, upstream of said ATR section and preferably between said methanation section and/or reverse water gas shift (rWGS) section, and said ATR section.

Aspect 6. The plant according to any one of the preceding aspects, wherein the syngas stream is fed directly from the syngas stage to the synthesis stage.

Aspect 7. The plant according to any one of aspects 1-6, wherein the plant comprises a post-conversion section, located between said syngas stage and said synthesis stage, and a stream comprising $CO_2$ to said post-conversion section, arranged to be mixed with the syngas stream between the syngas stage and the post-conversion section.

Aspect 8. The plant according to any one of the preceding aspects, further comprising a fifth feed of steam to the syngas stage.

Aspect 9. The plant according to any one of the preceding aspects, wherein the syngas stage comprises a methanation section and an autothermal reforming (ATR) section.

Aspect 10. The plant according to any one of the preceding aspects, wherein a part or all of the first feed is fed to the methanation section; and a part or all of the second feed is fed to the methanation section.

Aspect 11. The plant according to any one of the preceding aspects, wherein the methanation section comprises two or more methanation units, such as three or more methanation units.

Aspect 12. The plant according to aspect 11, wherein parts of the first feed comprising hydrogen are fed separately to different methanation units in the methanation section; or the entire first feed comprising hydrogen is fed to the methanation unit located furthest upstream in the methanation section.

Aspect 13. The plant according to any one of aspects 11-12, wherein parts of the second feed comprising carbon dioxide are fed separately to different methanation units in the methanation section; or the entire second feed comprising carbon dioxide is fed to the methanation unit located furthest upstream in the methanation section.

Aspect 14. The plant according to any one of aspects 11-13, wherein parts of the fourth feed comprising hydrocarbons are fed separately to different methanation units in the methanation section; or the entire fourth feed comprising hydrocarbons is fed to one methanation unit in the methanation section.

Aspect 15. The plant according to any one of aspects 11-14, wherein a part of the effluent from one methanation unit is cooled and recycled to the inlet of said methanation unit and/or to the inlet of any additional methanation units located upstream said one methanation unit.

Aspect 16. The plant according to any one of the preceding aspects, wherein the syngas stage comprises a reverse water gas shift (rWGS) section and an autothermal reforming (ATR) section.

Aspect 17. The plant according to any one of the preceding aspects, wherein a part or all of the first feed is fed to the rWGS section; and a part or all of the second feed is fed to the rWGS section.

Aspect 18. The plant according to any one of the preceding aspects, wherein the rWGS section comprises two or more rWGS units, such as three or more rWGS units.

Aspect 19. The plant according to aspect 18, wherein parts of the first feed comprising hydrogen are fed separately to different rWGS units in the rWGS section; or the entire first feed comprising hydrogen is fed to the reverse WGS unit located furthest upstream in the rWGS section.

Aspect 20. The plant according to any one of aspects 18-19, wherein parts of the second feed comprising carbon dioxide are fed separately to different rWGS units in the rWGS section; or the entire second feed comprising carbon dioxide is fed to the rWGS unit located furthest upstream in the rWGS section.

Aspect 21. The plant according to any one of the preceding aspects, wherein the syngas stream at the inlet of said synthesis stage has a hydrogen/carbon monoxide ratio in the range 1.00-4.00; preferably 1.50-3.00, more preferably 1.50-2.10.

Aspect 22. The plant according to any one of the preceding aspects, wherein the syngas stream at the outlet of said ATR section has a module, as defined above, between 1.90 and 2.30.

Aspect 23. The plant according to any one of the preceding aspects, wherein the ratio of $H_2:CO_2$ provided at the plant inlet is between 1.0-9.0, preferably 2.5-8.0, more preferably 3.0-7.0.

Aspect 24. The plant according to any one of the preceding aspects, wherein the synthesis stage is a Fischer-Tropsch (F-T) stage, and wherein the ratio of $H_2:CO_2$ provided at the plant inlet is between 1.0-9.0, preferably 2.5-8.0, more preferably 3.0-7.0.

Aspect 25. The plant according to any one of the preceding aspects, wherein the first feed consists essentially of hydrogen, i.e., over 75%, such as over 85%, preferably over 90%, more preferably over 95%, even more preferably over 99% of the first feed is hydrogen.

Aspect 26. The plant according to any one of the preceding aspects, wherein the second feed consists essentially of carbon dioxide, i.e., over 75%, such as over 85%, preferably over 90%, more preferably over 95%, even more preferably over 99% of the second feed is carbon dioxide.

Aspect 27. The plant according to any one of the preceding aspects, wherein the third feed consists essentially of oxygen, i.e., over 75% such as over 90% or over 95%, such as over 99% of the third feed is oxygen.

Aspect 28. The plant according to any one of aspects 5-27, wherein said fourth feed additionally comprises $CO_2$ and/or CO and/or $H_2$.

Aspect 29. The plant according to any one of the preceding aspects, wherein the third feed additionally comprises steam.

Aspect 30. The plant according to any one of the preceding aspects, wherein the synthesis stage is a Fischer-Tropsch (F-T) stage arranged to convert said syngas stream into at least a hydrocarbon product stream and a hydrocarbon-containing off-gas stream in the form of an F-T tail gas stream.

Aspect 31. The plant according to any one of the preceding aspects, wherein the synthesis stage is a Fischer-Tropsch (F-T) stage arranged to convert said syngas stream into at least a hydrocarbon product stream, being a diesel stream; and an LPG and/or a naphtha product stream, and wherein at least a portion of said LPG and/or a naphtha product stream is fed to the syngas stage.

Aspect 32. The plant according to aspect 31, wherein parts of said portion of said LPG and/or said naphtha product stream fed to the syngas stage are fed separately to different methanation units in the methanation section; or the entirety of said portion of said LPG and/or said naphtha product stream fed to the syngas stage is fed together to one methanation unit in the methanation section.

Aspect 33. The plant according to any one of aspects 1-28, in which the synthesis stage comprises a methanol synthesis stage arranged to provide at least a methanol product stream and a methanol off-gas stream, and wherein at least a portion of said methanol off-gas stream is fed to the syngas stage.

Aspect 34. The plant according to aspect 33, in which the synthesis stage further comprises a methanol-to-gasoline (MTG) synthesis stage arranged to receive the methanol product stream from the methanol synthesis stage and convert it to at least a gasoline stream and an LPG product stream, and wherein, optionally, a portion of said LPG product stream is fed to the syngas stage.

Aspect 35. The plant according to any one of the preceding aspects, wherein—when an LPG and/or a naphtha product stream is fed to the syngas stage—said plant further comprises a pre-reforming section, arranged in the LPG and/or naphtha product stream, upstream the syngas stage, and wherein a steam feed is arranged to be mixed with the LPG and/or a naphtha product stream, prior to being fed to said pre-reforming section.

Aspect 36. The plant according to any one of the preceding aspects, wherein effluent gas from the ATR section is arranged to heat the pre-reforming section.

Aspect 37. The plant according to any one of the preceding aspects, further comprising an electrolyser arranged to convert water or steam into at least a hydrogen-containing stream and an oxygen-containing stream, and wherein at least a part of said hydrogen-containing stream from the electrolyser is fed to the syngas stage as part or all of said first feed and/or wherein at least a part of said oxygen-containing stream from the electrolyser is fed to the syngas stage as part or all said third feed.

Aspect 38. The plant according to aspect 37, wherein the water or steam fed to the electrolyser is obtained from one or more units or stages in said plant.

Aspect 39. The plant according to any one of the preceding aspects, comprising a sixth feed comprising hydrogen to the syngas stream, upstream the synthesis stage.

Aspect 40. The plant according to aspect 39, wherein at least a part of said hydrogen-containing stream from the electrolyser is fed to the syngas stream, upstream the synthesis stage as said sixth feed comprising hydrogen.

Aspect 41. The plant according to any one of aspects 5-40, wherein said plant further comprises a hydrogenator arranged to hydrogenate the fourth feed, before said fourth feed enters the syngas stage.

Aspect 42. The plant according to any one of the preceding aspects, further comprising a hydrogen removal section, located between said syngas stage and said synthesis stage, and arranged to remove hydrogen from the syngas stream.

Aspect 43. The plant according to aspect 42, wherein at least a portion of the hydrogen removed from the syngas stream in said hydrogen removal section is compressed and fed as at least part of said first feed to the syngas stage.

Aspect 44. The plant according to any one of the preceding aspects, further comprising a carbon dioxide removal section, located between said syngas stage and said synthesis stage, and arranged to remove carbon dioxide from the syngas stream.

Aspect 45. The plant according to aspect 44, wherein at least a portion of the carbon dioxide removed from the syngas stream in said carbon dioxide removal section is compressed and fed as at least part of said second feed to the syngas stage.

Aspect 46. The plant according to any one of the preceding aspects, wherein the syngas stage additionally comprises a reverse water gas shift (rWGS) section and a methanation section; and wherein the reverse water gas shift (rWGS) section is arranged upstream the methanation section and the methanation section is arranged upstream the ATR section.

Aspect 47. The plant according to any one of the preceding aspects, wherein
the syngas stage (A) comprises a reverse water gas shift (rWGS) section (III) arranged in parallel to said ATR section (I);
wherein at least a portion of the first feed (1) and at least a portion of the second feed (2) are arranged to be fed to the rWGS section (III) and said rWGS section (III) is arranged to convert said at least a portion of the first feed (1) and at least a portion of the second feed (2) to a first syngas stream (40);
wherein a third feed (3) comprising hydrocarbons and a fourth feed (4) comprising oxygen are arranged to be fed to the ATR section (I); and wherein said ATR section (I) is arranged to convert said third feed (3) comprising oxygen and said fourth feed comprising hydrocarbons to a second syngas stream (50)
wherein the first syngas stream (41) from the rWGS section (III) is arranged to be combined with the second syngas stream (50) from the ATR section (I); and the combined syngas stream (100) is arranged to be fed to the synthesis stage (B).

Aspect 48. The plant according to aspect 47, wherein—before being combined with first and second syngas streams, the second syngas stream (50) from the ATR section (I) is arranged to provide at least a part of the energy required for the endothermic reaction in the rWGS section (III).

Aspect 49. The plant according to any one of aspects 1-46, wherein
the syngas stage (A) comprises a methanation section (II) arranged in parallel to said ATR section (I);
wherein at least a portion of the first feed (1) and at least a portion of the second feed (2) are arranged to be fed to the methanation section (II) and said rWGS section (III) is arranged to convert said at least a portion of the first feed (1) and at least a portion of the second feed (2) to a first syngas stream (31);
wherein a third feed (3) comprising hydrocarbons and a fourth feed (4) comprising oxygen are arranged to be fed to the ATR section (I); and wherein said ATR section (I) is arranged to convert said third feed (3) comprising oxygen and said fourth feed comprising hydrocarbons to a second syngas stream (50)
wherein the first syngas stream (31) from the methanation section (II) is arranged to be combined with the second syngas stream (50) from the ATR section (I); and the combined syngas stream (100) is arranged to be fed to the synthesis stage (B).

Aspect 50. A method for producing a product stream, said method comprising the steps of:
providing a plant as defined in any one of the preceding aspects;
supplying a first feed comprising hydrogen to the syngas stage;
supplying a second feed comprising carbon dioxide to the syngas stage;
supplying a third feed comprising oxygen to the ATR section; and
converting said first, second, third and fourth feeds in said syngas stage to a syngas stream and feeding said syngas stream to the synthesis stage;
converting said syngas stream in said synthesis stage into at least a product stream and a hydrocarbon-containing off-gas stream; and
feeding at least a portion of said hydrocarbon-containing off-gas stream or at least a portion of said product stream to the syngas stage as a fourth feed comprising hydrocarbons, upstream of said ATR section and preferably between the methanation section and/or the reverse water gas shift (rWGS) section and said ATR section.

Aspect 51. The method according to aspect 50, in which the synthesis stage is a Fischer-Tropsch (F-T) stage arranged to convert said syngas stream into at least a hydrocarbon product stream and a hydrocarbon-containing off-gas stream in the form of an F-T tail gas stream.

The invention claimed is:
1. A method for producing a product stream, said method comprising the steps of:
providing a plant (X), said plant comprising:
a. a syngas stage (A), said syngas stage (A) comprising a methanation section (II) and/or a reverse water gas shift (rWGS) section (III), and an autothermal reforming (ATR) section (I), wherein the methanation section (II) and/or the reverse water gas shift (rWGS) section (III) are arranged upstream the autothermal reforming (ATR) section (I); and
b. a synthesis stage (B),
wherein the plant does not comprise an external feed of hydrocarbons;
supplying a first feed (1) comprising hydrogen to the syngas stage (A);
supplying a second feed (2) comprising carbon dioxide to the syngas stage (A);
supplying a third feed (3) comprising oxygen to the ATR section; and
converting said first, second, third feeds and, optionally, a fourth feed, in said syngas stage (A) to a syngas stream and feeding said syngas stream to the synthesis stage (B);
converting said syngas stream in said synthesis stage (B) into at least a product stream and a hydrocarbon-containing off-gas stream; and
feeding at least a portion of said hydrocarbon-containing off-gas stream or at least a portion of said product stream to the syngas stage (A) as a fourth feed comprising hydrocarbons, upstream of said ATR section (I).

2. The method according to claim 1, in which the synthesis stage (B) is a Fischer-Tropsch (F-T) synthesis stage which converts said syngas stream into at least a hydrocarbon product stream and said hydrocarbon-containing off-gas stream in the form of an F-T tail gas stream.

3. The method according to claim 1, the method comprising:
feeding at least a portion of said hydrocarbon-containing off-gas stream or at least a portion of said product stream to the syngas stage (A) as a fourth feed comprising hydrocarbons, upstream of said ATR section (I) and between said methanation section (II) and/or said reverse water gas shift (rWGS) section (III), and said ATR section (I).

4. The method according to claim 1, the method comprising feeding the syngas stream directly from the syngas stage (A) to the synthesis stage (B).

5. The method according to claim 1, wherein the plant comprises a post-conversion section, located between said syngas stage (A) and said synthesis stage (B), the method further comprising:
feeding a stream comprising $CO_2$ to said post-conversion section and by mixing the stream comprising $CO_2$ with the syngas stream between the syngas stage (A) and the post-conversion section.

6. The method according to claim 1, further comprising: feeding a fifth feed (5) of steam to the syngas stage (A).

7. The method according to claim 1, wherein the syngas stage (A) consists of a methanation section (II) arranged upstream an autothermal reforming (ATR) section (I).

8. The method according to claim 1, the method comprising feeding a part or all of the first feed (1) to the methanation section (II); and feeding a part or all of the second feed (2) to the methanation section (II).

9. The method according to claim 1, wherein the methanation section (II) comprises two or more methanation units.

10. The method according to claim 1, wherein the syngas stream at the inlet of said synthesis stage (B) has a hydrogen/carbon monoxide ratio in a range of 1.0-4.0.

11. The method according to claim 1, wherein a ratio of $H_2:CO_2$ provided at the plant inlet is between 1.0-9.0.

12. The method according to claim 11, wherein the synthesis stage (B) is an Fischer-Tropsch (F-T) synthesis stage and the $H_2:CO_2$-ratio at the plant inlet is in a range of 3.0-7.0.

13. The method according to claim 1, in which the synthesis stage (B) comprises a methanol synthesis stage arranged to provide at least a methanol product stream and a methanol off-gas stream,
the method further comprising:
feeding at least a portion of said methanol off-gas stream to the syngas stage (A).

14. The method according to claim 1, the plant further comprising an electrolyser arranged to convert water or steam into at least a hydrogen-containing stream and an oxygen-containing stream,
the method further comprising:
feeding at least a part of said hydrogen-containing stream from the electrolyser to the syngas stage (A) as part or all of said first feed and/or feeding at least a part of said oxygen-containing stream from the electrolyser to the syngas stage (A) as part or all said third feed.

15. The method according to claim 1, further comprising feeding a sixth feed of hydrogen to the syngas stream, upstream the synthesis stage (B).

16. The method according to claim 1, further comprising feeding a part or all of the first feed to the methanation section and/or reverse water gas shift (rWGS) section; and feeding a part or all of the second feed to the methanation section and/or reverse water gas shift (rWGS) section.

17. The method according to claim 3, wherein the syngas stage (A) comprises a reverse water gas shift (rWGS) section (III) arranged in parallel to said ATR section (I), the method comprising:
feeding at least a portion of the first feed (1) and at least a portion of the second feed (2) to the rWGS section (III) and converting in said rWGS section (III) said at least a portion of the first feed (1) and at least a portion of the second feed (2) to a first syngas stream;
converting in said ATR section (I) said third feed (3) comprising oxygen and said fourth feed comprising hydrocarbons to a second syngas stream;
combining the first syngas stream from the rWGS section (III) with the second syngas stream from the ATR section (I); and feeding the combined syngas stream to the synthesis stage (B).

18. The method according to claim 17, wherein, before being combined with the first syngas stream, the syngas stream from the ATR section (I) provides at least a part of the energy required for the endothermic reaction in the rWGS section (III).

19. The method according to claim 3, wherein the syngas stage (A) comprises a methanation section (II) arranged in parallel to said ATR section (I), the method comprising:
feeding at least a portion of the first feed (1) and at least a portion of the second feed (2) to the methanation section (II) and converting in said methanation section (II) said at least a portion of the first feed (1) and at least a portion of the second feed (2) to a first syngas stream.
converting said ATR section (I) said third feed (3) comprising oxygen and said fourth feed comprising hydrocarbons to a second syngas stream;
combining the first syngas stream from the methanation section (II) with the second syngas stream from the ATR section (I); and the feeding the combined syngas stream to the synthesis stage (B).

20. A method for producing a product stream, said method comprising the steps of:
supplying a first feed (1) comprising hydrogen to a syngas stage (A), said syngas stage (A) comprising a methanation section (II) and/or a reverse water gas shift (rWGS) section (III), and an autothermal reforming (ATR) section (I), wherein the methanation section (II) and/or the reverse water gas shift (rWGS) section (III) are arranged upstream the autothermal reforming (ATR) section (I);
supplying a second feed (2) comprising carbon dioxide to the syngas stage (A);
supplying a third feed (3) comprising oxygen to the ATR section; and
converting said first, second, third feeds and, optionally, a fourth feed, in said syngas stage (A) to a syngas stream and feeding said syngas stream to a synthesis stage (B);
converting said syngas stream in said synthesis stage (B) into at least a product stream and a hydrocarbon-containing off-gas stream; and
feeding at least a portion of said hydrocarbon-containing off-gas stream or at least a portion of said product stream to the syngas stage (A) as a fourth feed comprising hydrocarbons, upstream of said ATR section (I), wherein the process does not comprise an external feed of hydrocarbons.

* * * * *